(12) United States Patent
Hirano et al.

(10) Patent No.: US 7,155,507 B2
(45) Date of Patent: Dec. 26, 2006

(54) METHOD AND SYSTEM FOR PROVIDING ENVIRONMENTAL INFORMATION ON NETWORK

(75) Inventors: Motohisa Hirano, Tokyo (JP); Tadashi Katoh, Tokorozawa (JP); Takeshi Toriyama, Fuchu (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 875 days.

(21) Appl. No.: 09/815,420

(22) Filed: Mar. 22, 2001

(65) Prior Publication Data

US 2001/0029535 A1    Oct. 11, 2001

(30) Foreign Application Priority Data

Mar. 25, 2000    (JP)    ............................ P2000-128638
Nov. 21, 2000    (JP)    ............................ P2000-354553

(51) Int. Cl.
G06F 15/173    (2006.01)

(52) U.S. Cl. ........................................ 709/224; 706/930
(58) Field of Classification Search ................ 709/203, 709/208, 217, 224; 706/930; 600/529
See application file for complete search history.

(56) References Cited

U.S. PATENT DOCUMENTS

| | | | | |
|---|---|---|---|---|
| 5,831,876 A | * | 11/1998 | Orr et al. ........................ | 703/6 |
| 5,892,690 A | * | 4/1999 | Boatman et al. ............ | 700/276 |
| 6,023,223 A | * | 2/2000 | Baxter, Jr. .................. | 340/531 |
| 6,031,455 A | * | 2/2000 | Grube et al. ............ | 340/539.26 |
| 6,230,080 B1 | * | 5/2001 | Lee et al. .................... | 700/275 |
| 6,231,519 B1 | * | 5/2001 | Blants et al. ................ | 600/529 |
| 6,288,646 B1 | * | 9/2001 | Skardon ..................... | 340/627 |
| 6,466,133 B1 | * | 10/2002 | Skardon ..................... | 340/627 |
| 2002/0119769 A1 | * | 8/2002 | Heinonen et al. ........... | 455/422 |

FOREIGN PATENT DOCUMENTS

| | | |
|---|---|---|
| EP | 0 989 503 A1 | 3/2000 |
| JP | 09-091358 | 4/1997 |

(Continued)

OTHER PUBLICATIONS

K. Nakano, "Towards distribution of environmental information", NTT Technology Journal, Aug. 1, 2000, vol. 12, No. 8, pp. 20-23, Electric Communication Society, Japan.

(Continued)

*Primary Examiner*—Marc D. Thompson
*Assistant Examiner*—Joseph Maniwang
(74) *Attorney, Agent, or Firm*—Brenda O. Holmes; Kilpatrick Stockton LLP

(57) ABSTRACT

A scheme for providing environmental information to users is disclosed. In this scheme, environmental information is measured automatically by each of a plurality of environment sensors arranged at a plurality of regions, and the environmental information measured by each environment sensor is collected automatically to a base device, and stored at the base device. Then, the environmental information is processed at the base device according to a user information of an individual user, and processed environmental information is provided from the base device to the individual user through a network connecting the users and the base device.

26 Claims, 17 Drawing Sheets

FOREIGN PATENT DOCUMENTS

| | | |
|---|---|---|
| JP | 10-124601 | 5/1998 |
| JP | 11-046193 | 2/1999 |
| JP | 11-066081 | 3/1999 |
| JP | 11-103490 | 4/1999 |
| JP | 11-109047 | 4/1999 |
| JP | 11-250383 | 9/1999 |
| JP | 11-252670 | 9/1999 |
| JP | 2000-020556 | 1/2000 |
| JP | 2000-040086 | 2/2000 |
| JP | 2000-193469 | 7/2000 |
| JP | 2000-295375 | 10/2000 |

OTHER PUBLICATIONS

Yuichiro Mori, "Starting Real Time Programming with RT-Linux", Trans TECH, Jan. 1, 2000, pp. 179-184, No. 2 of vol. 9, Shoeisha Co., Ltd., Japan.

* cited by examiner

AREA INFORMATION FOR POLLEN SEASON (STATE)

EXEMPLARY CORRESPONDENCE TABLE FOR SYMPTOMS & AMOUNTS (FIVE LEVELS)

| POLLEN ALLERGY SYMPTOMS | AMOUNT OF POLLENS |
|---|---|
| TERRIBLE | VERY LARGE |
| BAD | LARGE |
| SLIGHTLY BAD | SLIGHTLY LARGE |
| NERVOUS | NOT SO LARGE |
| NO SYMPTOM | SMALL |

EXEMPLARY CORRESPONDENCE TABLE FOR
WARNINGS & AMOUNTS (FIVE LEVELS)

| POLLEN WARNINGS | AMOUNT OF POLLENS |
|---|---|
| TERRIBLE | VERY LARGE |
| BAD | LARGE |
| SLIGHTLY BAD | SLIGHTLY LARGE |
| NERVOUS | NOT SO LARGE |
| NO SYMPTOM | SMALL |

METHOD AND SYSTEM FOR PROVIDING ENVIRONMENTAL INFORMATION ON NETWORK

BACKGROUND OF THE INVENTION

1. Field of the Invention

The present invention relates to environmental information providing method and system which are suitable for assisting a network on which environmental information is to be disclosed and shared, such as pollen information providing method and system for detecting amounts of pollens scattered at a plurality of regions, applying information processing according to needs, and providing pollen information through a communication system.

2. Description of the Background Art

Conventional sensors for handling environmental information over a wide range include a radio-sonde or the like which collects weather information such as temperature, humidity, atmospheric pressure, and wind direction while moving according to a preset condition and transmits the weather information, and a rain gauge, wind gauge or the like at the meteorological observatory which passively acquires observational information and transmits the observational information. With these conventional sensors, it is difficult to realize the long term measurement while automatically changing the measurement condition such as measurement position or frequency according to a state of the environmental information at a target region.

Also, the conventionally provided environmental information has been a physical quantity such as temperature. For this reason, the environmental information accounting for a personal sensitivity has not been provided in practice. For example, there is an individual difference in a relationship between the pollen count in the environment and the onset of the pollen allergy (pollinosis), but there has been no practice for providing tailor-made information that accounts for such an individual difference.

More specifically, the scattering of pollens is a severe threat to a person suffering the pollen allergy so that it is important for each such person to take his/her own measures at an early stage, such as learning an arrival of the pollen scattering season earlier or learning regions where a large amount of pollens are scattering earlier, predicting an influence from these regions to the own residence area or an arrival timing at the own residence area, and avoiding visits to these regions as much as possible or taking preventive medicine in some cases.

Also, the symptoms of the pollen allergy are different for different pollen allergic persons so that there can be persons who are very sensitive to pollens even in a state where only a small amount of pollens are scattering as well as persons who have no problem with the scattering of only a small amount of pollens. As such, different individuals have different sensitivities with respect to the scattering of pollens and there is an individual difference in a relationship between the amount of pollens scattering in the atmosphere and the onset of the pollen allergy.

Conventionally, there has been a system for observing the weather information such as temperature, humidity, atmospheric pressure, and wind direction and disclosing the weather information as the environmental information, but there has been no system for measuring and collecting the amounts of pollens scattering in the atmosphere and distributing such information.

Also, the conventionally provided environmental information is a physical quantity such as temperature in general, and there has been no practice for providing the environmental information that depends on the personal sensitivity. Namely, there is an individual difference in a relationship between the amount of pollens in the atmosphere and the onset of the pollen allergy, but there has been no practice for providing one-to-one information for each individual by setting a one-to-one correspondence between the amount of pollens and the pollen allergy of each individual.

Moreover, there has been no practice for providing information on a macroscopic change of a base line of the amount of scattering pollens or regional distributions of base line states rather than a temporary amount of scattering pollens at a given timing.

As described, conventionally, there is a problem that no appropriate system for measuring, collecting and distributing the amount of pollens scattering in the atmosphere is available so that the pollen allergic person could not have taken appropriate measures at an early stage, and there are demands for a system that measures and provides the amount of pollens scattering in the atmosphere.

Also, as described above, different individuals exhibit different pollen allergy symptoms in relation to the amount of pollens scattering in the atmosphere so that what is really needed for the pollen allergic person is a one-to-one information for each individual that is provided by setting one-to-one correspondence between each individual and the pollen allergy symptom of each individual in relation to the amount of pollens, but there is a problem that there has been no practice for providing such a one-to-one information conventionally.

Moreover, it can be beneficial for the pollen allergic persons to have information on a macroscopic change of a base line of the amount of scattering pollens or regional distributions of base line states rather than a temporary amount of scattering pollens at a given timing, but there is a problem that there has been no practice for providing such information.

SUMMARY OF THE INVENTION

It is therefore an object of the present invention to provide environmental information providing method and system which are capable of assisting a network on which the environmental information obtained by environmental sensors or the like is to be disclosed and shared.

It is another object of the present invention to provide environmental information providing method and system which are capable of providing not only a constantly changing real time information on pollens but also information on a macroscopic state change and regional distributions of the amount of scattering pollens, as well as a one-to-one information on the amount of pollens and the pollen allergy symptom that varies from one individual to another, on a network.

According to one aspect of the present invention there is provided a method for providing environmental information to users, comprising the steps of: measuring environmental information automatically by each of a plurality of environment sensors arranged at a plurality of regions; collecting the environmental information measured by each environment sensor automatically to a base device; storing the environmental information collected from the plurality of environment sensors at the base device; processing the environmental information at the base device according to a user information of an individual user; and providing processed environmental information from the base device to the individual user through a network connecting the users and the base device.

According to another aspect of the present invention there is provided an environmental information providing system, comprising: a plurality of environment sensors arranged at a plurality of regions and configured to measure environmental information automatically; a first communication unit configured to collect the environmental information measured by each environment sensor automatically; a database configured to store the environmental information collected from the plurality of environment sensors by the first communication unit; a processing unit configured to process the environmental information stored in the database according to a user information of an individual user; and a second communication unit configured to provide processed environmental information obtained by the processing unit to the individual user through a network connecting the users and the environmental information providing system.

According to another aspect of the present invention there is provided a method for providing an environmental information service from a service system to users, comprising the steps of: offering processed environmental information obtained by processing environmental information collected from a plurality of environment sensors arranged at a plurality of regions, according to a user information of an individual user, for accesses from the users through a network connecting the users and the service system; and providing the processed environmental information from the service system to the individual user through the network.

Other features and advantages of the present invention will become apparent from the following description taken in conjunction with the accompanying drawings.

DETAILED DESCRIPTION OF THE PREFERRED EMBODIMENTS

Figure 1:
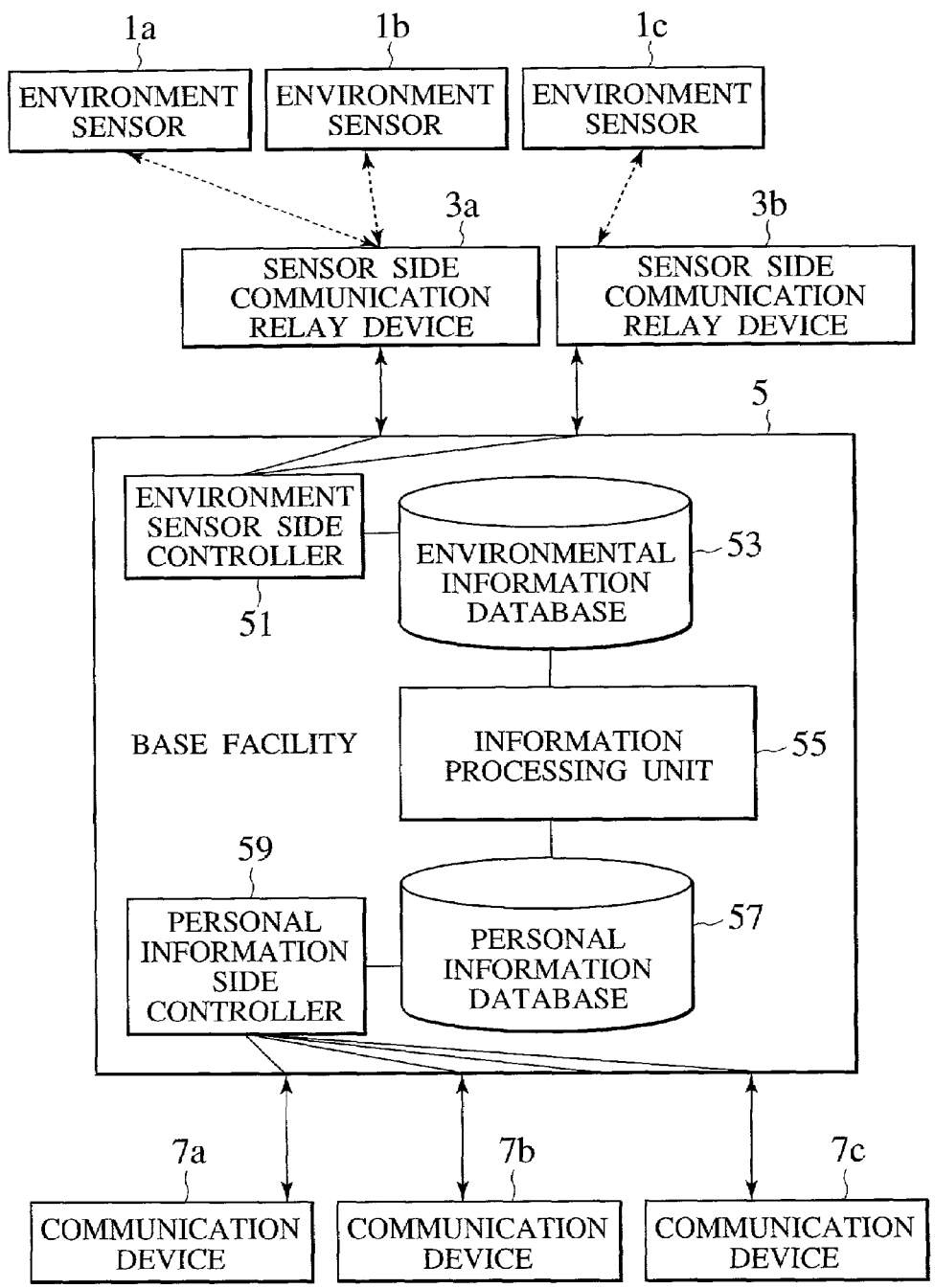
FIG. 1 is a block diagram showing an exemplary configuration of an environmental information providing system according to the first embodiment of the present invention.

Referring now to FIG. 1 to FIG. 6, the first embodiment of environmental information providing method and system according to the present invention will be described in detail.

First, the major features of this embodiment will be summarized briefly.

In this embodiment, the real time environmental information measured by a group of sensors arranged in the environment is automatically communicated to a device for storing environmental data within a base facility via a communication system combining wireless and wired telephones. Here the real time environmental information implies information that is automatically detected by sensors such as measured values of temperature, pollen count, etc. The environmental information can be regional information such as the pollen count which can vary from one plain to another that are separated by a mountain range. Such a regional environmental information is acquired in this embodiment. When the regional environmental information changes violently, the corresponding measurement function is improved.

The sensors arranged in the environment have a built-in radio communication device. Using this device, each sensor transmits the environmental information under a prescribed condition set up in advance, and each sensor can also transmit the environmental information under a condition based on commands given through communication channels.

The sensors carry out radio communications so that there is a large degree of freedom regarding places for arranging the sensors. Also, a relay device is provided with respect to a sensor or a group of sensors, where the relay device carries out radio communications with the sensors and wire communications with the base facility device. In this way, it becomes possible to acquire the measured environmental information conveniently. For example, the environmental information can be acquired and processed automatically without requiring any manual operations so as to follow the change such as an increase or decrease of the pollen count during the night time. Also, the environmental information such as the pollen count at a place where each user is currently located can be acquired easily by using a portable telephone or the like.

The base facility device automatically processes the environmental information obtained from the sensors via the communication system by using an information processing unit. The information processing unit carries out processing including the storing of the environmental information, the statistical processing such as averaging and correlation of values, and the simulation using the physical laws and computational methods. The environmental information measured by the sensors is processed by the information processing unit to become information useful for living such as the estimated value of the environmental information at a place where the individual user is located.

The information processing unit has a function for automatically updating the measurement condition setting of the sensors through the communication system according to the environmental information obtained by the sensors and its information processing result. For example, in the case where one of the sensors for detecting pollens measures a large amount of pollens, a shorter measurement interval can be set for the other related sensors, or a change of the location can be commanded to a sensor provided on a moving body such as vehicle, airship, etc.

The environmental information data and values obtained by processing the environmental information data that are stored in the base facility device can be acquired conveniently via the communication system by using an information device such as a portable telephone.

The environmental information at a location registered in the personal information data in advance or a location detected by a personal information side controller of the base facility according to information accompanying communications can be acquired by the information device such as a portable telephone via the communication system as the processing result of the information processing unit.

The personal information regarding a sensitivity of the individual user with respect to the environment such as a level of the pollen allergy can be stored into the personal information data within the base facility from the information device via the communication system. Using this information, the environmental information that can be acquired by the individual user can be made suitable for the sensitivity of the individual user with respect to the environment, such that it becomes possible to acquire the information accounting for the individual difference such as that in the symptom of the pollen allergy, for example.

To the personal information data obtained by communications, information on a personal identification number of the user, a location of the information device at a time of communications, etc., is attached. Such information related to the privacy of the individual user is protected by using a password, encryption, etc.

The environmental information data and the personal information data are processed by the information processing unit as a result of an access from the information device such as a portable telephone and an automatic activation of the information processing unit, and the processing result is received via the communication system. For example, there is an individual difference in a relationship between the symptom of the pollen allergy and the pollen count, and it is possible to provide a push information for warning a level of the pollen allergy for a specific individual according to the personal information of that individual stored in the base facility device based on a prediction of the pollen count at a given time and a given place. In the case of such a push information, the charge can be weighted accordingly.

Now, this embodiment will be described in further detail with references to the drawings.

FIG. 1 shows an overall configuration of a bidirectional environment monitoring system that is one embodiment of an environmental information providing system for realizing an environmental information providing method according to the present invention.

The bidirectional environment monitoring system of FIG. 1 comprises environment sensors 1 including three environment sensors 1a, 1b and 1c in this example, sensor side communication relay devices 3 including two sensor side communication relay devices 3a and 3b in this example, a base facility 5, and communication devices 7 including three communication devices 7a, 7b and 7c in this example.

Figure 2:
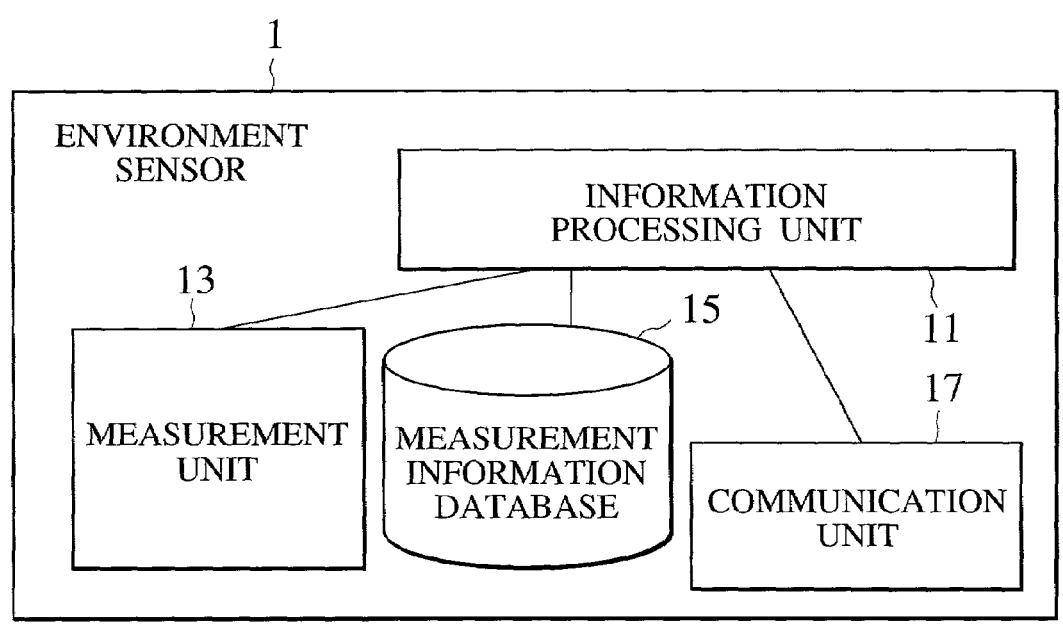
FIG. 2 is a block diagram showing an exemplary configuration of an environment sensor used in the environmental information providing system of FIG. 1.

Each environment sensor 1 for measuring environmental information has a configuration shown in FIG. 2, which comprises an information processing unit 11, a measurement unit 13, a measurement information database 15, and a communication unit 17.

The base facility 5 further comprises an environment sensor side controller 51, an environmental information database 53, an information processing unit 55, a personal information database 57, and a personal information side controller 59.

Next, the operation and the processing procedure in this embodiment will be described with references to FIG. 1 to FIG. 6.

Figure 3:
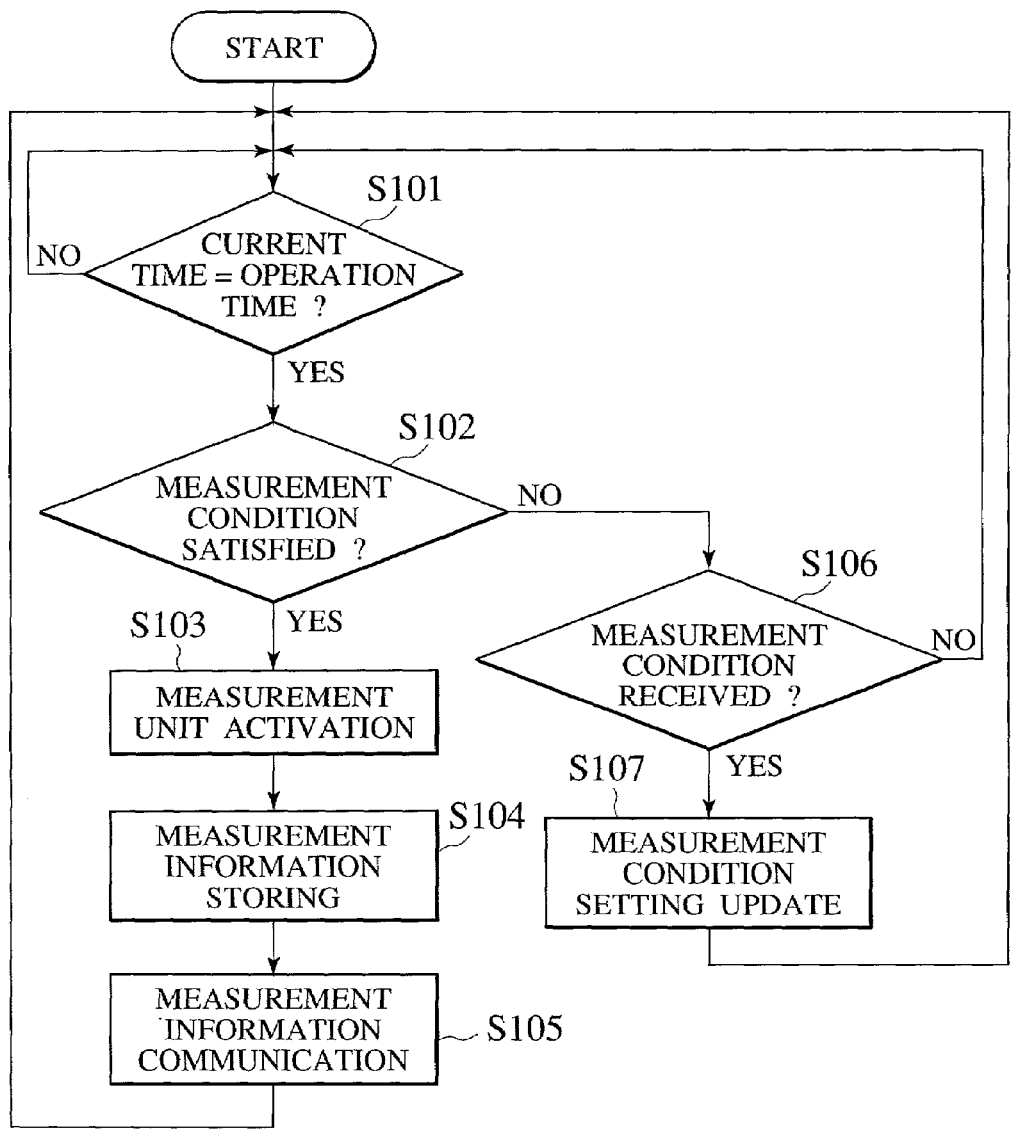
FIG. 3 is a flow chart showing a processing procedure for measuring and collecting environmental information in the environmental information providing system of FIG. 1.

First, the operation and the processing procedure of the environment sensor 1 will be described with reference to FIG. 3. The measurement unit 13 measures an amount of pollens, volcanic gas, etc., as the environmental information. The communication unit 17 carries out bidirectional communications with the sensor side communication relay devices 3a and 3b, through radio channels or telephone lines, for example.

The measurement information database 15 is provided on recording media such as hard disks, etc. In the measurement information database 15, a prescribed measurement condition is set up in advance, and the information processing unit 11 checks whether it is an operation time or not at a constant time interval (step S101). When it is the operation time, the information processing unit 11 checks whether the prescribed measurement condition is satisfied or not (step S102), and if it is satisfied the information processing unit 11 activates the measurement unit 13 (step S103) and stores measurement data received from the measurement unit 13 into the measurement information database 15 (step S104). The measurement data stored in the measurement information database 15 are then communicated to the sensor side communication relay devices 3a and 3b through radio channels by the communication unit 17 according to a setting of the information processing unit 11 (step S105).

On the other hand, when the measurement condition is not satisfied at the step S102 and the communication unit 17 receives a new measurement condition through communications (step S106 YES), the information processing unit 11 updates the measurement condition setting by using the new measurement condition (step S107).

The group of environment sensors 1a. 1b and 1c that are arranged in a target region carry out bidirectional communications with the environment sensor side controller 51 in the base facility 5 via the sensor side communication relay devices 3a and 3b. In this system, communications are carried out through radio channels between the environment sensors 1a, 1b and 1c and the sensor side communication relay devices 3a and 3b, and through telephone lines between the sensor side communication relay devices 3a and 3b and the environment sensor side controller 51. With this combination, the environment sensors 1 can be arranged at remote locations in a wide range. For example, in the case of measuring the amount of pollens, the environment sensors 1 can be easily arranged at many cedar forests in a mountainous region.

Figure 4:
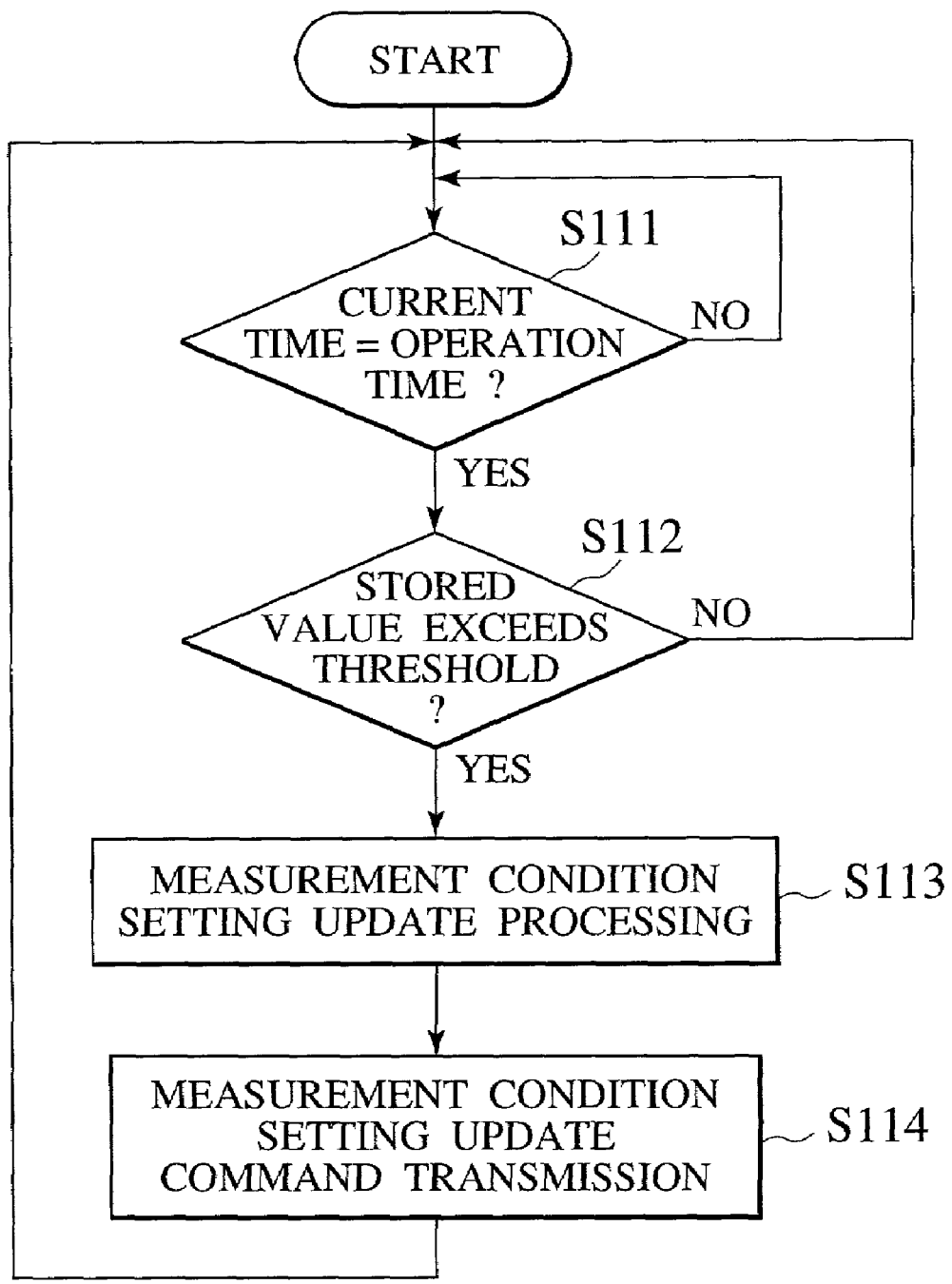
FIG. 4 is a flow chart showing a processing procedure for updating a measurement condition setting of an environment sensor in the environmental information providing system of FIG. 1.
Figure 5:
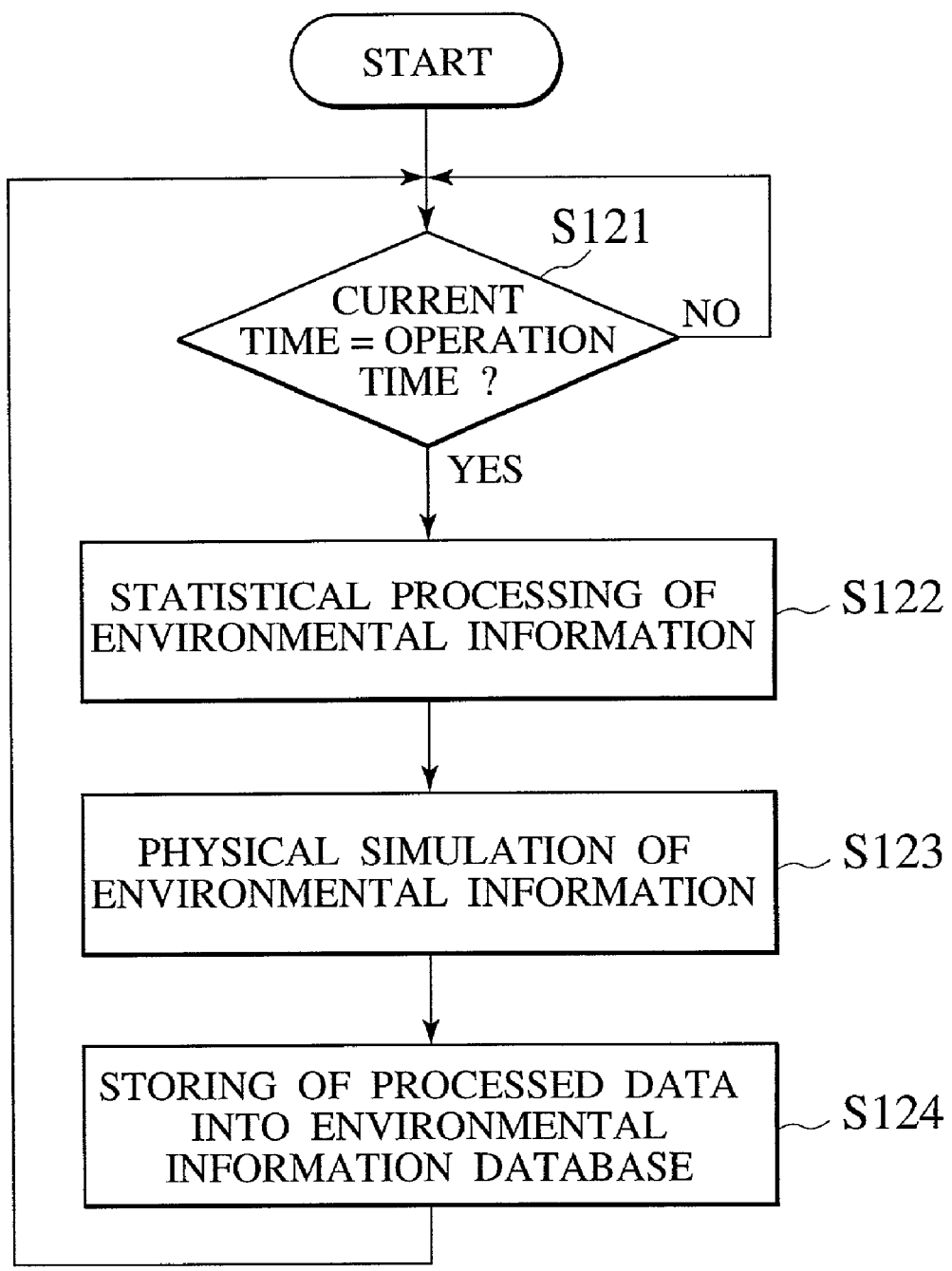
FIG. 5 is a flow chart showing a processing procedure for processing environmental information in the environmental information providing system of FIG. 1.
Figure 6:
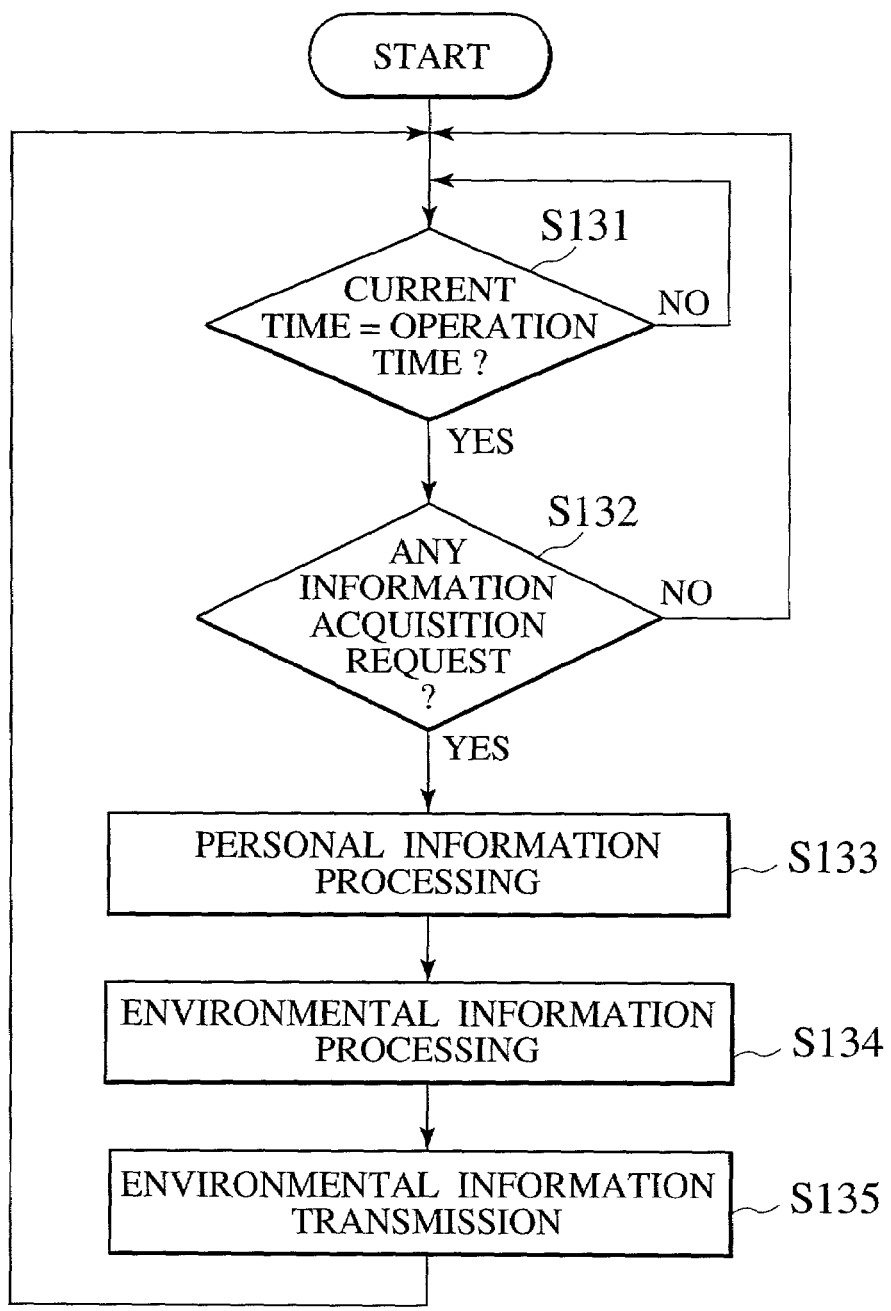
FIG. 6 is a flow chart showing a processing procedure for providing environmental information to users in the environmental information providing system of FIG. 1.

Next, the operation and the processing procedure of the base facility 5 will be described with reference to FIG. 4 to FIG. 6. The environmental sensor side controller 51 stores the received environmental information into the environmental information database 53 provided on recording media within the base facility 5. The environmental information database 53 stores the environmental information such as measurement positions, measurement times, measured values, etc., of the environment sensors 1a, 1b and 1c. In addition, geographical data such as locations of cedar forests in the case of handling pollens are also stored in the environmental information database 53 on the recording media.

The information processing unit 55 provided in the base facility 5 checks whether it is an operation time or not at a constant time interval (step S111). When it is the operation time, the information processing unit 55 checks the environmental information database 53, and when a value of the environmental information for some environmental sensor 1 exceeds a prescribed threshold value set in advance (step S112 YES), the information processing unit 55 carries out a measurement condition setting update processing with respect to the group of environment sensors 1a, 1b and 1c according to a scheme specified in the information processing unit 55 (step S113), and transmits commands for the measurement condition setting update through telephone lines, for example (step S114).

For example, in the case of the pollen sensors arranged in a mountainous region, normally one out of several sensors is operated to carry out the measurement in view of the limited battery power, but when some sensor measures a large amount of pollens, all the sensors in that region are commanded to carry out the measurement. Also, when a compact pilotless observation airship with the environment sensor mounted thereon is provided in that region, this airship is commanded to move to the leeward.

The information processing unit 55 also checks whether it is an operation time or not at a constant time interval (step S121), and when it is the operation time, the information processing unit 55 carries out the statistical processing such as averaging or correlation with respect to values stored in the environmental information database 53 (step S122). Also, the information processing unit 55 carries out a simulation according to the physical laws governing the environmental information (step S123). In this way, the information processing unit 55 estimates the distribution of the environmental information over the entire target region, and stores the processed data also into the environmental information database 53 (step 124).

For example, the amount of scattering pollens in nearby cedar forests is estimated according to the scattering laws from the pollen count measured by the environment sensor, and the distribution of the pollen count over an entire plain region is estimated from the estimated value and a numerical simulation based on the physical laws such as those for movement and scattering of pollens due to air stream and precipitation of pollens due to gravity or interpolations of values from a plurality of environment sensors at different locations. Also, a prediction of the future values is made by using a time series data of the values from the environment sensors.

When the value of such a processed data exceeds a prescribed threshold, the information processing unit 55 also transmits commands for the measurement condition setting update to the environment sensors 1 similarly as in the steps S112 and S114 described above.

The environmental information can be conveniently acquired from the communication devices 7a, 7b and 7c through telephone lines. Requests for the environmental information acquisition are sent from the communication devices 7a, 7b and 7c through the personal information side controller 59, and stored into the personal information database 57 on the recording media in the base facility 5.

From the communication devices 7a, 7b and 7c, data regarding sensitivities of users with respect to the environment can be stored into the personal information database 57. For example, an information indicating that a level of the pollen allergy of a user is the fourth level in an evaluation scale with five levels, from the communication device 7a to the personal information database 57. The information processing unit 55 detects a location of the communication device 7a in advance from a location registered in the personal information database 57 or an information accompanying the communication, and attaches information on the pollen count at a time and a place corresponding to the communication to the information to be stored. The information processing unit 55 processes the information stored in the personal information database 57 in order to account for the personal pollen allergy information in the information on the pollen count.

The information processing unit 55 also checks whether it is an operation time or not at a constant time interval (step S131), and when it is the operation time, the information processing unit 55 checks the personal information database 57. When there is a request for the environmental information acquisition in the personal information database 57 (step S132 YES), the information processing unit 55 carries out the processing of the personal information stored in the personal information database 57 (step S133), obtains the environmental information corresponding to that personal information by processing the information or the processed information stored in the environmental information database 53 (step S134), and transmits that environmental information to one of the communication devices 7a, 7b and 7c that issued that request (step S135).

For example, when a threshold with respect to the environmental information is set up for each individual separately in the personal information database 57 from the communication devices 7a, 7b and 7c, and when the environmental information in a region of one of the communication devices 7a, 7b and 7c exceeds its threshold, the information processing unit 55 automatically transmits an alarm to the corresponding one of the communication devices 7a, 7b and 7c as a tailor-made information.

Note that, in the above, it is assumed that one communication device 7 is used in one-to-one correspondence with one user, but a user using the communication device 7a can also acquire the information from the different communication devices 7b and 7c by changing the setting in the personal information database 57 that is protected by using a password or the like.

Also, at a time of providing the environmental information by communications, it is easily possible to charge the user appropriately. For example, at a time of providing the environmental information by communications, the user can be charged appropriately according to whether it is push or pull, or according to the amount of processing of the environmental information. Namely, there is an individual difference in a relationship between the symptom of the pollen allergy and the pollen count, and in the case of the push information for warning a level of the pollen allergy for a specific individual according to the personal information of that individual stored in the base facility 5 based on a prediction of the pollen count at a given time and a given place, the charge can be weighted accordingly.

Note that the environmental information on the base facility 5 may contain not only audio data but also image data and text data, and a user may use information devices including a telephone, a portable telephone, a computer, etc. It is also possible to utilize an access by a user to a home page displayed by the base facility 5 through the Internet.

As described, according to this embodiment, the environmental information is collected from a plurality of environment sensors and analyzed, while a prediction value of the environmental information is simulated using the weather information, so that it becomes possible to deliver or provide the environmental information suitable for each individual with respect to a plurality of individual users, and thereby it becomes possible for a user to acquire the environmental information suitable for each individual any time anywhere, by using a fixed telephone, a portable telephone or a portable terminal, or a computer or a television connected to a communication channel. In addition, the system can appropriately select a communication scheme to be utilized from those using telephone lines or radio channels (portable/automobile telephone, satellite portable/automobile telephone, the so called "i-mode" of the portable telephone, etc.) according to the circumstances.

As a result, the user can acquire the regional environmental information as well as its future prediction value of his/her own place and other places appropriately and easily, so that it becomes possible for a pollen allergic user to set up appropriate plans for future outing, for example.

Note that this environmental information providing system can be realized in a form of an environmental information providing program which can be recorded on a recording medium, such that the environmental information providing program can be distributed in forms recording media.

Note also that the above embodiment is directed to an exemplary case for collecting the environmental information from the environment sensors such as pollen sesnsors that can detect pollens, but the present invention is not necessarily limited to this specific case, and can be applied to any of the following cases, for example:

(1) A service for providing the collected environmental information in real time as information for unspecified many users (regardless of whether they have contracts or not);

(2) A service for simulating the future prediction value of the environmental information from the collected environmental information weather information and related information (traffic information, calamity information, administrative information, etc.), and providing it in real time as information for unspecified many users;

(3) A service for providing in real time information suitable for each individual based on the collected environmental information or the simulated future prediction value, such as (a) information at a location registered by the individual user in advance, (b) information at a current (or future) location of the individual user deduced from communications with the individual user, or (c) information specific to the individual user such as pollen (warning) information according to the information on a level of the pollen allergy in the case where the individual user is pollen allergic; and (4) A service for providing information obtained by statistically processing information on the symptom of the pollen allergy that is returned from the individual user in the case where the information to be provided in the pollen information.

Also, the information to be handled includes the personal information so that it is possible to employ the encryption or the authentication systems according to the need in addition to the protection using a password or the like.

Also, the recipients of services by this system are not necessarily limited to individual users, and can be hospitals, meteorological societies, environmental organizations, regional administrative governmental facilities or organizations, or users of the Internet or the like.

As described, according to this embodiment, it becomes possible to acquire the regional environmental information obtained by the environment sensors or the like and its prediction value appropriately and easily, so that it is possible to assist the network on which the environmental information is to be disclosed and shared.

Referring now to FIG. 7 to FIG. 19, the second embodiment of environmental information providing method and system according to the present invention will be described in detail.

Figure 7:
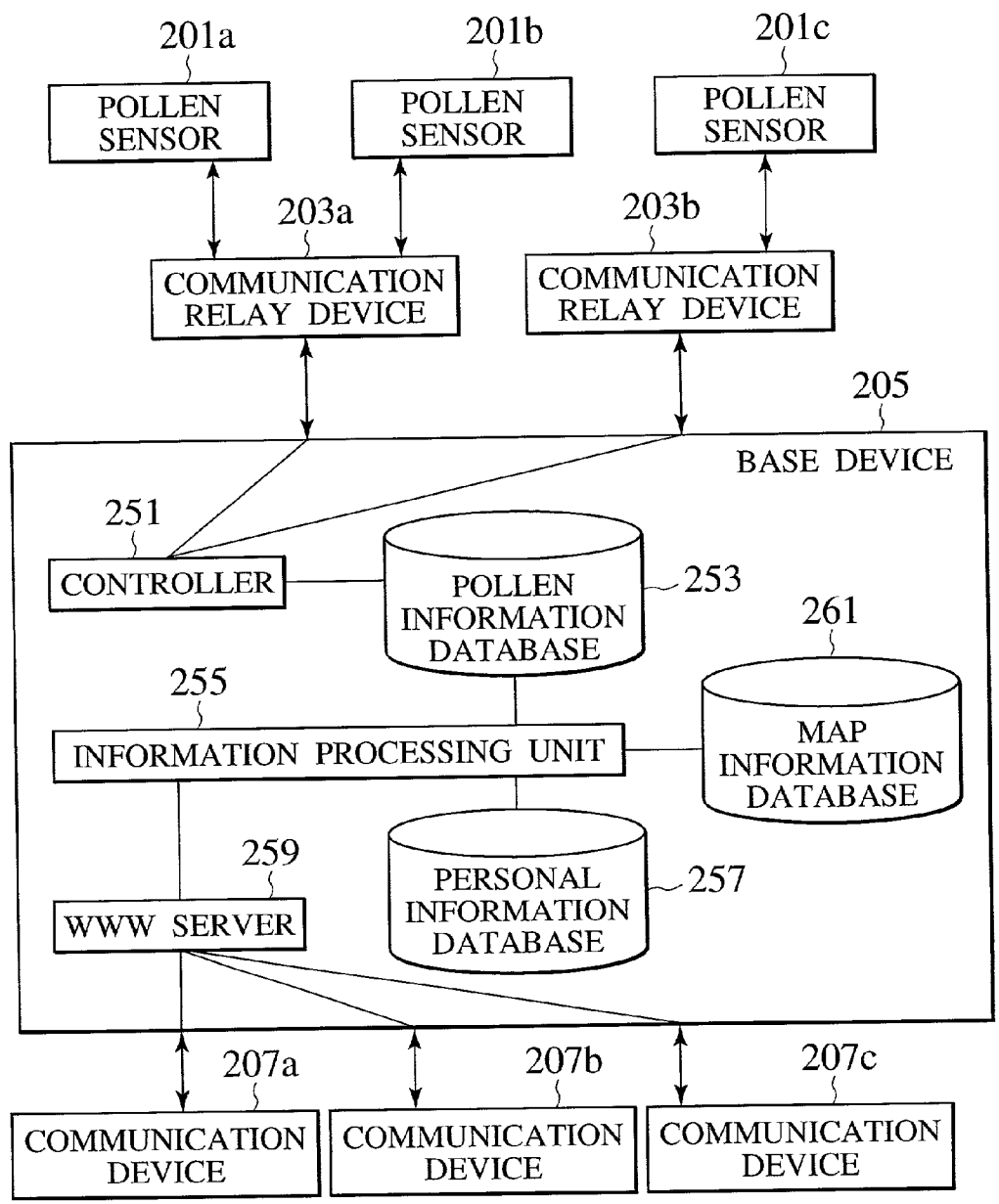
FIG. 7 is a block diagram showing an exemplary configuration of an environmental information providing system according to the second embodiment of the present invention.

FIG. 7 shows an overall configuration of a pollen information providing system that is another embodiment of an environmental information providing system for realizing an environmental information providing method according to the present invention.

The pollen information providing system of FIG. 7 comprises: a plurality of pollen sensors 201a, 201b and 201c, to be arranged at a plurality of regions where pollens are likely to be scattered, for detecting the number of pollens scattering in each region, i.e., the amount of pollens, and outputting the pollen amount information for each region; a plurality of communication relay devices 203a and 203b connected with the plurality of pollen sensors 201 through communication channels such as radio channels, for receiving the pollen amount information outputted from the pollen sensors 201 and relaying the pollen amount information while amplifying it, for example; a base device 205 connected with the communication relay devices 203 through communication channels, for receiving the pollen amount information from the pollen sensors 201 relayed by the communication relay devices 203, processing the received pollen amount information and providing various pollen information; and a plurality of communication devices 7 including three communication devices 207a, 207b and 207c in forms of portable telephones that are connected with the base device 205 through communication systems including the Internet or the like, for example.

Note that FIG. 7 shows an exemplary case involving only three pollen sensors 201*a*, 201*b* and 201*c*, two communication relay devices 203*a* and 203*b*, and three communication devices 207*a*, 207*b* and 207*c*, but the present invention is not limited to this specific case.

The base device 205 further comprises: a pollen information database 253 for storing the pollen amount information for each region detected by the plurality of pollen sensors 201; a map information database 261 for storing map information for regions where the pollen sensors 201 are arranged, regions where pollens are likely to be scattered, or a whole nation such as Japan; a personal information database 257 for storing personal information for individual users who require the pollen information; a controller 251 for receiving the pollen amount information from the communication relay devices 203 and storing the pollen amount information into the pollen information database 253; an information processing unit 255 for information processing the pollen amount information stored in the pollen information database 253; and a WWW server 259 connected with the communication devices 207 through communication systems such as the Internet or the like, for providing various pollen information in response to accesses from the communication devices 207. Note that the personal information stored in the personal information database 257 is protected by the security technique.

Figure 8:
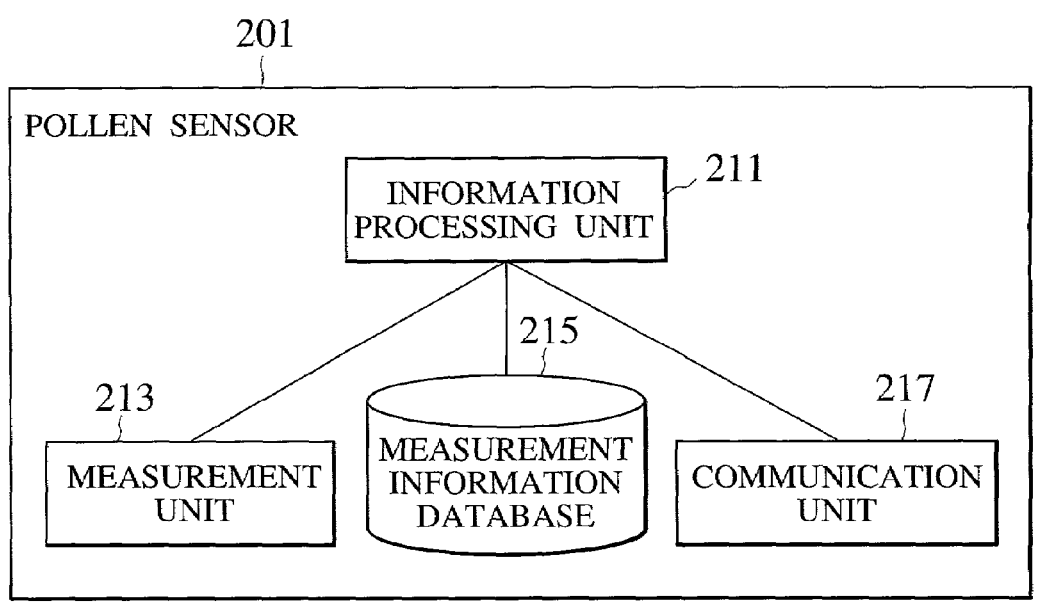
FIG. 8 is a block diagram showing an exemplary configuration of an environment sensor used in the environmental information providing system of FIG. 7.

Each pollen sensor 201 has a configuration shown in FIG. 8, which comprises a measurement unit 213 for detecting and measuring the pollen amount as the pollen count, an information processing unit 211 for information processing the pollen amount measured by the measurement unit 213, a measurement information database 215 for storing the pollen amount information obtained by the information processing at the information processing unit 211 along with date and time information, for example, and a communication unit 217 for transmitting the pollen amount information stored in the measurement information database 215 to the base device 205 via the communication relay devices 203.

Next, the various operations of this pollen information providing system of FIG. 7 will be described with references to FIG. 9 to FIG. 17.

Figure 9:
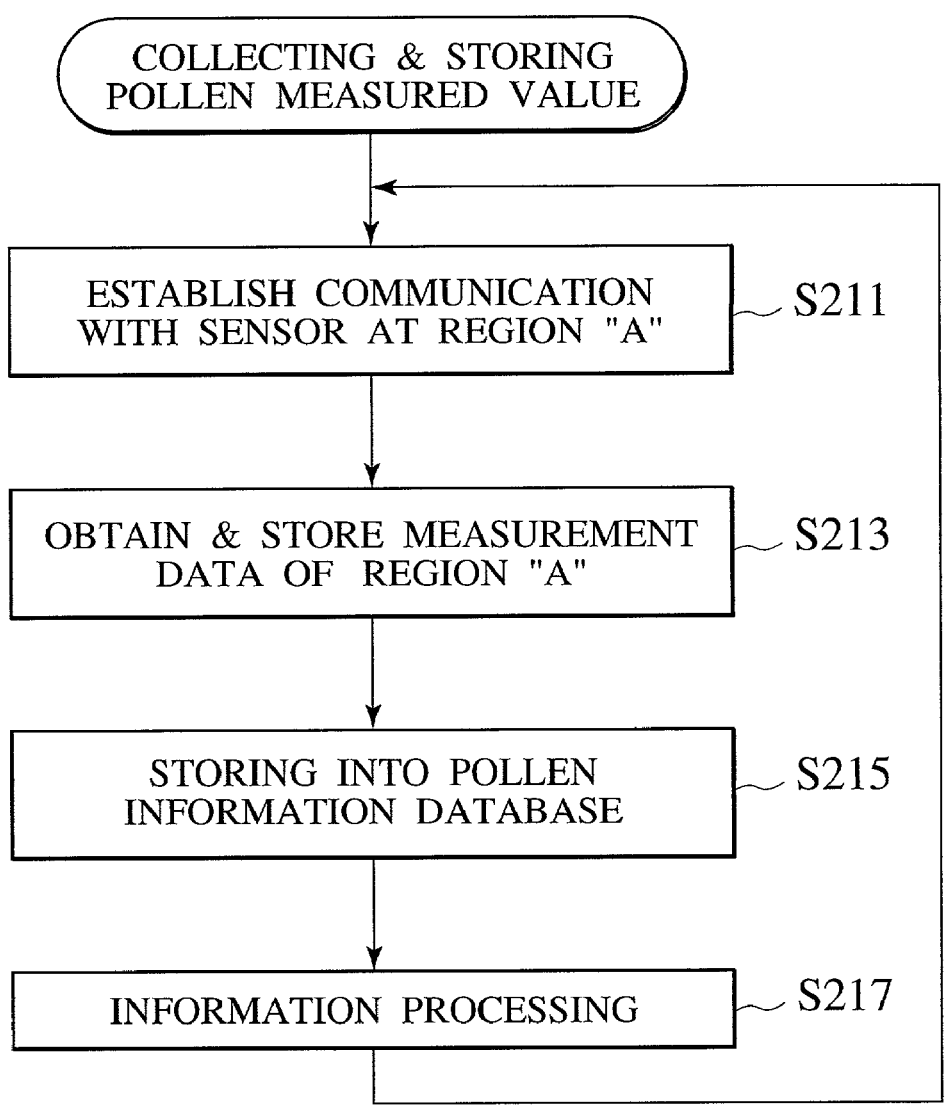
FIG. 9 is a flow chart showing a processing procedure for measuring and collecting environmental information in the environmental information providing system of FIG. 7.

First, with reference to FIG. 9, the processing for measuring the pollen amount at the pollen sensor 201 and collecting and storing the pollen amount measurement values at the base device 205 will be described.

The base device 205 makes an access to the pollen sensor 201 of a region A among the plurality of pollen sensors 201 through the communication relay device 203 first, and establishes communication with this pollen sensor 201 of the region A (step S211).

Note here that the present invention is not limited to this particular case of establishing communication with respect to the pollen sensor 201 from the base device 205 through the communication relay device 203 under the control of the base device 205, and it is also possible to use a procedure in which the communication relay device 203 carries out communication with the controller 251 of the base device 205 so as to establish communication between the pollen sensor 201 and the base device 205 through the communication relay device 203 under the control of the communication relay device 203, or a procedure in which the pollen sensor 201 establishes communication with respect to the base device 205 through the communication relay device 203 under the control of the pollen sensor 201.

As described above, when the communication channel is established between the base device 205 and the pollen sensor 201 of the region A through the communication relay device 203, the base device 205 obtains the measurement data of the pollen amount detected by the pollen sensor 201 of the region A, and stores this pollen amount measurement data along with the measurement region information of this pollen sensor 201 and the measurement date and time information into the pollen information database 253 under the control of the controller 251 (steps S213, S215). Then, the information processing unit 255 carries out the information processing of the pollen amount information stored in the pollen information database 253 at a constant time interval, for example, such as the statistical information processing including the integration processing and the averaging processing for each region and each time, for example (step S217).

The pollen amount information collected at the base device 205 and stored in the pollen information database 253 as described above can be acquired from the communication device 207 such as a portable telephone of the user by accessing the WWW server 259 of the base device 205 through a communication system such as the Internet. In addition, the user can similarly acquire the pollen amount information for a region specified from the communication device 207, for a region registered into the personal information database 257 in advance, or for a region closest from a location detected according to information accompanying the communication, by using the communication device 207 through the communication system.

Note that the acquisition of the pollen amount measurement data at the pollen sensor 201 is realized, for example, by setting an observation condition in the measurement information database 215 in advance, activating the measurement unit 213 from the information processing unit 211 at a constant time interval according to this observation condition and thereby carrying out the measurement of the pollen amount at the measurement unit 213, and storing the measured pollen amount measurement data into the measurement information database 215. Then, the measurement data stored in the measurement information database 215 is transmitted from the communication unit 217 through the communication channel such as radio channel to the communication relay device 203 under the control of the information processing unit 211.

Note here that the present invention is not limited to this particular case of transmitting the pollen amount measurement data from the pollen sensor 201 to the base device 205 at a constant time interval under the control of the pollen sensor 201, and it is also possible to use a procedure in which the base device 205 makes an access to the pollen sensor 201 at a prescribed timing, makes a request for transmission of the pollen amount measurement data to the pollen sensor 201, and acquires the pollen amount measurement data transmitted from the pollen sensor 201 in response to this request.

Next, with reference to FIG. 10, the processing for judging an arrival of a pollen season at the base device 205 will be described.

The pollens are not always being scattered so that there are a state in which the pollen amount is small and a state in which the pollen amount is large. Here, the state in which the pollen amount is small will be referred to as an offset state while the state in which the pollen amount is large will be referred to as an onset state. Then, a period for which the state remains as the onset state with a large pollen amount will be referred to as a pollen season. When the pollen season during which the state remains as the onset state with a large pollen amount arrives, there is a need for the pollen allergic persons to be cautious. Consequently, it is important to accurately judge whether the pollen season has arrived or not, and the processing of FIG. 10 is devised to judge such an arrival of the pollen season.

Figure 10:
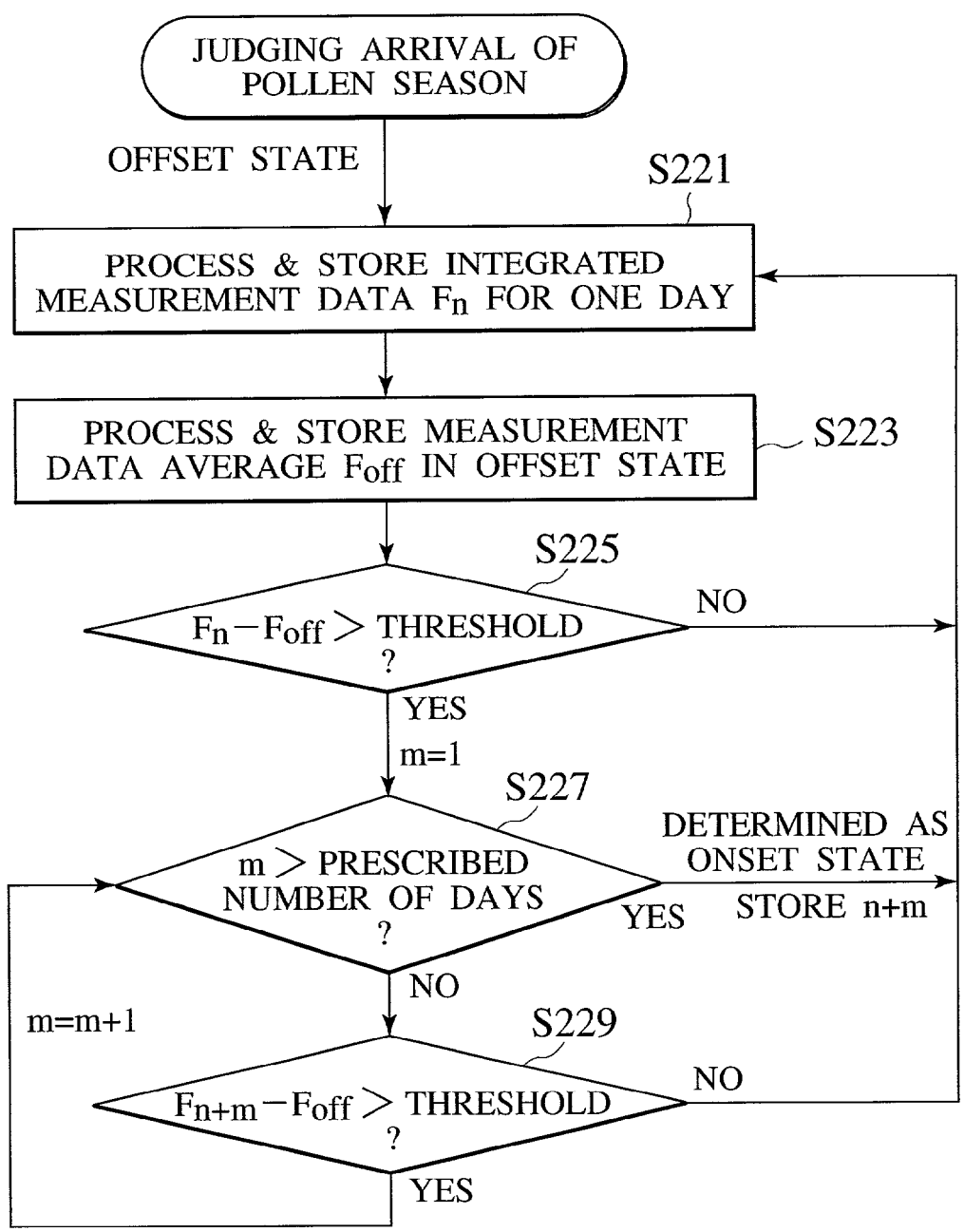
FIG. 10 is a flow chart showing a processing procedure for judging an arrival of a pollen season in the environmental information providing system of FIG. 7.

In the processing of FIG. 10, it is assumed that the state is in the offset state with a small pollen amount initially, and in this offset state, the controller 251 of the base device 205 integrates the pollen amounts collected from the pollen sensor 201 for each region in units of one day everyday, and stores this integrated value Fn of the pollen amount per day along with the date information into the pollen information database 253 (step S221).

Also, at the base device 205, an average value Foff of the pollen amount measurement data for the past one month, for example, in the offset state with a small pollen amount at each region is calculated as a regular value in the offset state, and this regular value Foff in the offset state is stored into the pollen information database 253 (step S223). Then, the variation of the integrated value Fn per day with respect to the regular value Foff in the offset state is monitored, and the arrival of the pollen season is judged, i.e., it is decided as the onset state, when the integrated value Fn per day exceeds the regular value Foff in the offset state by more than a prescribed threshold, for example, that is, when the increase in the pollen amount per day by more than a prescribed threshold has continued for a prescribed number days or more (three days or more, for example).

Note that the threshold is set to be an integer multiple of the regular value Foff, more specifically three times the regular value Foff, for example. Also, the regular value Foff described above is also referred to as a base line in the offset state, and similarly a regular value Fon in the onset state to be described below is also referred to as a base line in the onset state.

At the next step S225, whether a value obtained by subtracting the regular value Foff in the offset state from the integrated value Fn of the pollen amount per day calculated at the step S221 is greater than the threshold or not is judged, and if it is not greater than the threshold, the processing returns to the step S221 to repeat the same processing, whereas if it is greater than the threshold, that is when the pollen amount per day has increased to a value greater than the regular value Foff in the offset state plus the threshold, a parameter m for counting the number of days is set to 1, and whether this parameter m is greater than the prescribed number of days (three days, for example) described above or not is judged (step S227). When this parameter m is not greater than the prescribed number of days as a result of this judgement, the integrated value Fn+m of the pollen amount per day for the next day is read out from the pollen information database 253, and whether a value obtained by subtracting the regular value Foff in the offset state from the integrated value Fn+m of the pollen amount per day is greater than the threshold or not is judged (step S229).

When it is not greater than the threshold as a result of this judgement, that is, when the pollen amount has not increased continuously, the processing returns to the step S221 to repeat the same processing from the start, whereas when it is greater than the threshold, the parameter m for counting the number of days is incremented by one, and the processing returns to the step S227 and whether the incremented value of this parameter m is greater than the prescribed number of days or not is judged. This processing is repeated until the number of days for having a value greater than the threshold exceeds the prescribed number of days continuously. Then, when the number of days for having a value greater than the threshold exceeds the prescribed number of days, such as three days for example, it is decided as the onset state, that is, it is judged as an arrival of the pollen season, and the date n+m of the arrival of the pollen season is stored into the pollen information database 253. In this way, the arrival of the pollen season can be judged.

Next, with reference to FIG. 11, the processing for judging an end of a pollen season at the base device 205 will be described. Note that, in this processing of FIG. 11, the regular value Fon in the onset state is used in place of the regular value Foff in the offset state. This regular value Fon in the onset state is an average value of the pollen amount measurement data for the past one month, for example, in the onset state with a large pollen amount, similarly as the regular value Foff in the offset state.

Figure 11:
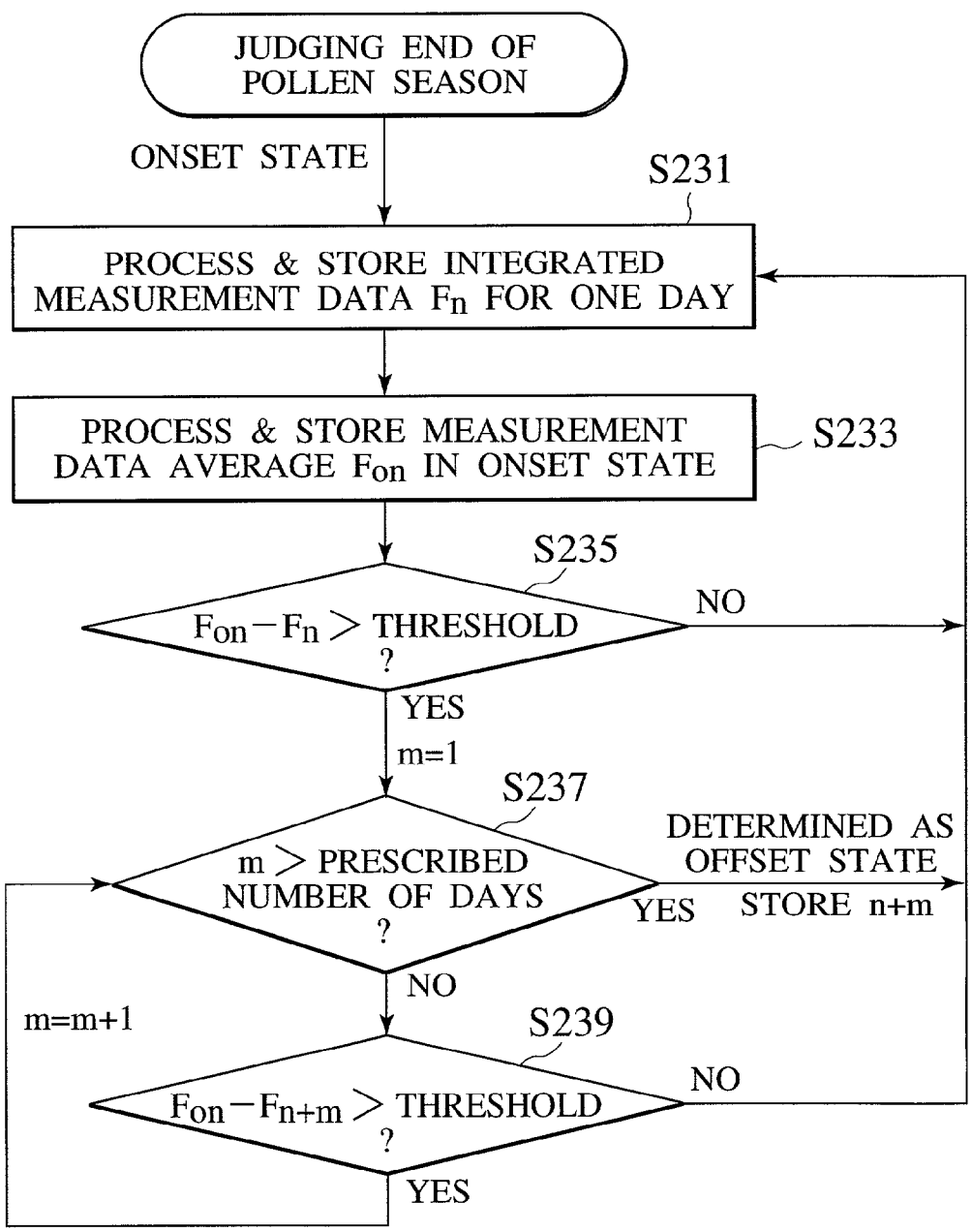
FIG. 11 is a flow chart showing a processing procedure for judging an end of a pollen season in the environmental information providing system of FIG. 7.

In the processing of FIG. 11, it is assumed that the state is in the onset state with a large pollen amount initially, and in this onset state, the controller 251 of the base device 205 integrates the pollen amounts collected from the pollen sensor 201 for each region in units of one day everyday, and stores this integrated value Fn of the pollen amount per day along with the date information into the pollen information database 253 (step S231).

Also, at the base device 205, an average value Fon of the pollen amount measurement data for the past one month, for example, in the offset state with a small pollen amount at each region is calculated as a regular value in the onset state, and this regular value Fon in the onset state is stored into the pollen information database 253 (step S233). Then, the variation, more specifically the decrease, of the integrated value Fn per day with respect to the regular value Fon in the onset state is monitored, and whether a value obtained by subtracting the integrated value Fn of the pollen amount per day from the regular value Fon in the onset state is greater than the prescribed threshold or not is judged (step S235). Here, the threshold is set to the same value as in the case of the offset state described above.

When a value obtained by subtracting the regular value Fon in the onset state from the integrated value Fn of the pollen amount per day is not greater than the threshold as a result of the judgement at the step S235, the processing returns to the step S231 to repeat the same processing, whereas if it is greater than the threshold, that is when the pollen amount per day has decreased to a value less than the regular value Fon in the onset state plus the threshold, a parameter m for counting the number of days is set to 1, and whether this parameter m is greater than the prescribed number of days (three days, for example) or not is judged (step S237). When this parameter m is not greater than the prescribed number of days as a result of this judgement, the integrated value Fn+m of the pollen amount per day for the next day is read out from the pollen information database 253, and whether a value obtained by subtracting the integrated value Fn+m of the pollen amount per day from the regular value Fon in the onset state is greater than the threshold or not is judged (step S239).

When it is not greater than the threshold as a result of this judgement, that is, when the pollen amount has not decreased continuously, the processing returns to the step S231 to repeat the same processing from the start, whereas when it is greater than the threshold, the parameter m for counting the number of days is incremented by one, and the processing returns to the step S237 and whether the incremented value of this parameter m is greater than the prescribed number of days or not is judged. This processing is repeated until the number of days for having a value greater than the threshold exceeds the prescribed number of days continuously. Then, when the number of days for having a value greater than the threshold exceeds the prescribed number of days, such as three days for example, it is decided as the offset state, that is, it is judged as an end of the pollen season, and the date n+m of the end of the pollen season is stored into the pollen information database 253. In this way, the end of the pollen season can be judged.

Figure 12:
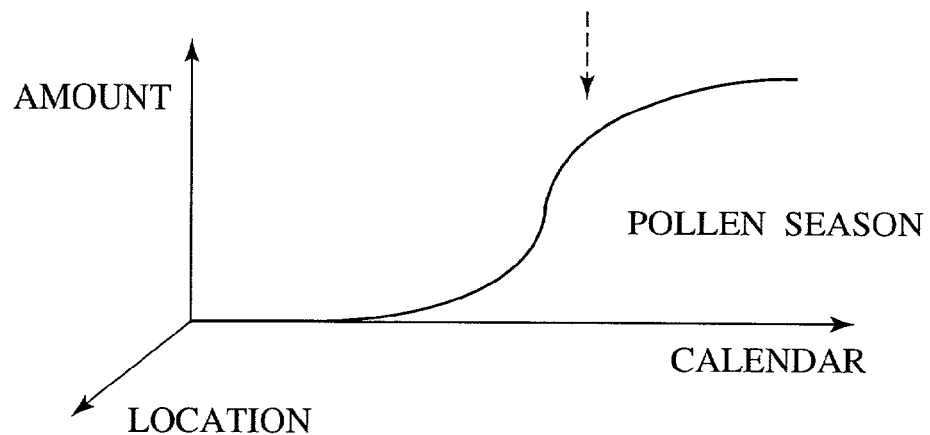
FIG. 12 is a diagram showing an exemplary pollen distribution area information that can be used in the environmental information providing system of FIG. 7.

Also, by obtaining the regular value Fon in the onset state and the regular value Foff in the offset state as described above for each region stored in the map information database 261, and displaying the regular value Fon or Foff obtained for each region on the map, it is possible to obtain a pollen distribution area information in which areas where the regular value Fon with a large pollen amount is distributed and areas where the regular value Foff with a small pollen amount is distributed are clearly shown on the map as shown in FIG. 12. Then, it can be seen that areas where the regular value Fon with a large pollen amount is distributed are areas that are in the pollen season.

Figure 13:
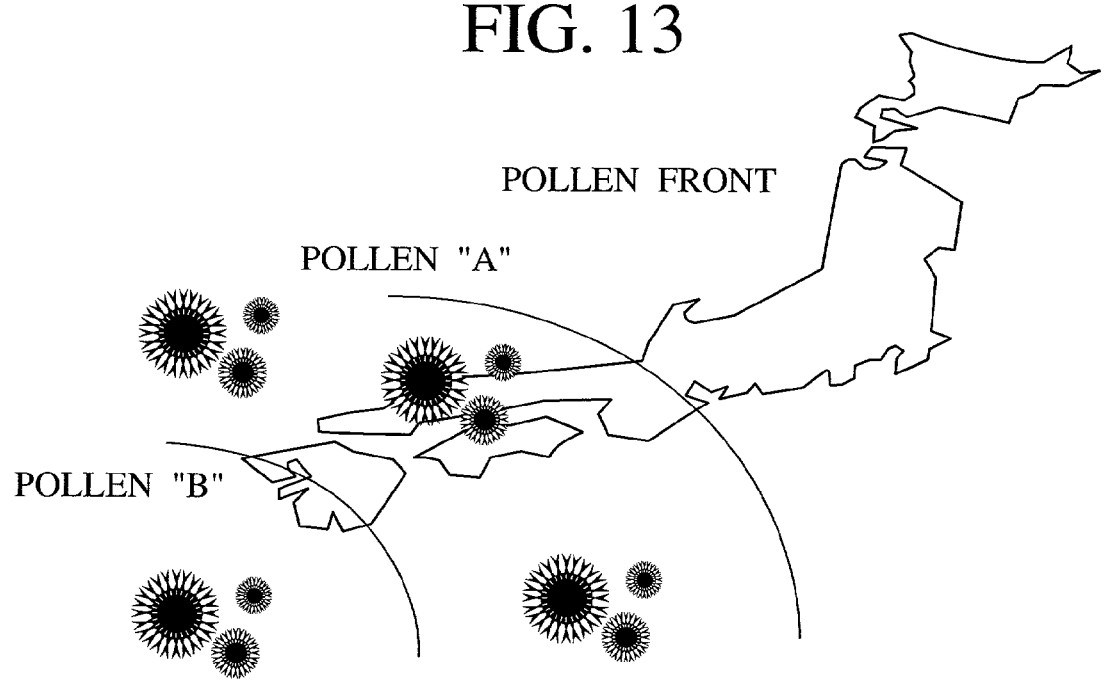
FIG. 13 is a diagram showing an exemplary pollen border information that can be used in the environmental information providing system of FIG. 7.

These areas that are in the pollen season will steadily changes as the time elapses, and a border of the areas in the pollen season, that is a border between areas in which the regular value Fon with a large pollen amount is distributed and areas in which the regular value Foff with a small pollen amount is distributed in the pollen distribution area information indicates a pollen front as shown in FIG. 13, which is similar to the "sakura" (cherry blossom) front or the "baiu" (seasonal rain) front used in the weather information in Japan, and this pollen front steadily moves as the time elapses.

Namely, the pollen distribution area information is obtained by judging whether the state of each region is the state with a small pollen amount or the state with a large pollen amount, and visualizing areas with little pollens and areas with many pollens in a form of a map according to the judged state of each region, where areas with many pollens are the areas in the pollen season, and a border between areas with little pollens and areas with many pollens is the pollen front which provides a pollen border information. Consequently, by visually displaying these pollen distribution area information and the pollen border information in a form of the pollen front on the map and providing them to the user through the communication system, it becomes possible for the user to know the areas with many pollens accurately, and take appropriate preventive measures according to the need.

Note that the information processing unit 255 of the base device 205 can retrieve information regarding whether the pollen amount at each region is in the onset state or in the offset state from the pollen information database 253, so that by registering a region of interest, a communication address, and a notification reservation, etc., for the user in advance, it is possible to retrieve information regarding whether the pollen amount at that region is in the onset state or in the offset state, and notify the pollen season warning to the user's address or the like that is registered by the user when it becomes the onset state voluntarily (as a push information).

Next, with references to FIG. 14 to FIG. 17, the processing for registering and providing a one-to-one information at the base device 205 will be described.

Figures 14, 15:
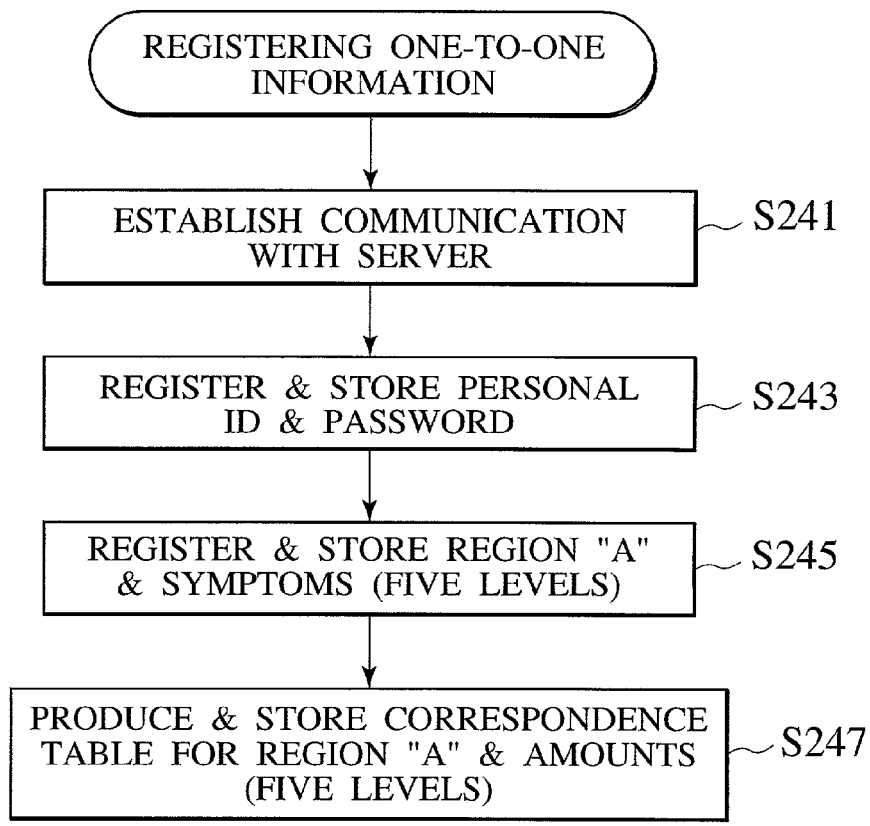
FIG. 14 is a flow chart showing a processing procedure for registering one-to-one information in the environmental information providing system of FIG. 7.
FIG. 15 is a diagram showing an exemplary correspondence table used in the processing for registering one-to-one information shown in FIG. 14.

In the registration and providing of the one-to-one information, an access from the user using the communication device 207 is accepted at the WWW server 259, and a user's personal ID, a user specified region name information, and a correspondence table indicating a correspondence between a plurality of pollen allergy symptoms of the user and a plurality of pollen amount levels as shown in FIG. 15, for example, which are entered by the user, are received and stored into the personal information database 257, while the pollen amount at each region detected by the pollen sensor 201 is information processed by the information processing unit 255 to classify it as one of the plurality of pollen amount levels and stored into the pollen information database 253 as the pollen amount level of each region.

Note that, in the correspondence table of FIG. 15, the plurality of pollen allergy symptoms include "terrible", "very bad", "slightly bad", "nervous" and "no symptom", while the plurality of pollen amount levels include "very large", "large", "slightly large", "not so large" and "small", and the correspondences among them which are specific to the user are indicated by lines drawn between them.

Then, when the user makes an access to the WWW server 259 of the base device 205 by using the communication device 207, and enters the personal ID and the password, the pollen information database 253 is searched through according to the user specified region name information, to acquire the pollen amount level at the user specified region, and also the personal information database 257 is searched through according to the personal ID of the user to read out the correspondence table of the user and acquire the pollen allergy symptom corresponding to the pollen amount level at the user specified region from the read out correspondence table, and then this pollen allergy symptom is notified to the user as a pollen warning information.

More specifically, the registration of the one-to-one information will be described with reference to FIG. 14.

The user makes an access to the WWW server 259 of the base device 205 through the telephone line and the Internet, for example, from the communication device 207, and establishes communication with the WWW server 259 (step S241). Then, the personal ID and the password of the user are registered, and stored into the personal information database 257 of the base device 205 (step S243).

Also, the user registers information on a user specified region whose pollen information should be notified, such as a region A for example, and the pollen amount levels corresponding to the pollen allergy symptoms of the user, and this information is also stored into the personal information database 257 (step S245). At the base device 205, the information processing unit 255 produces the correspondence table indicating the correspondence between the user's pollen allergy symptoms and the pollen amount levels at the region A as shown in FIG. 15 according to the stored information, and stores this correspondence table into the personal information database 257 (step S247).

Next, the providing of the one-to-one information which takes place after the correspondence table of the user is produced and stored into the personal information database 257 as described above, will be described with reference to FIG. 16.

The pollen information stored in the pollen information database 253 of the base device 205 is disclosed to each user through the Internet by the WWW server 259. The user makes an access to the WWW server 259 of the base device 205 through the telephone line and the Internet, for example, from the communication device 207, and establishes communication with the WWW server 259 (step S251), and when the user enters the personal ID and the password, the information processing unit 255 of the base device 205 carries out the matching of the password (step S253). When it is confirmed that it is a legitimate user as a result of the password matching, the information processing unit 255 searches through the personal information database 257 according to the personal ID of the user, and obtains the correspondence table indicating the correspondence between the user's pollen allergy symptoms and the pollen amount levels at the user specified region A (step S255).

Figures 16, 17:
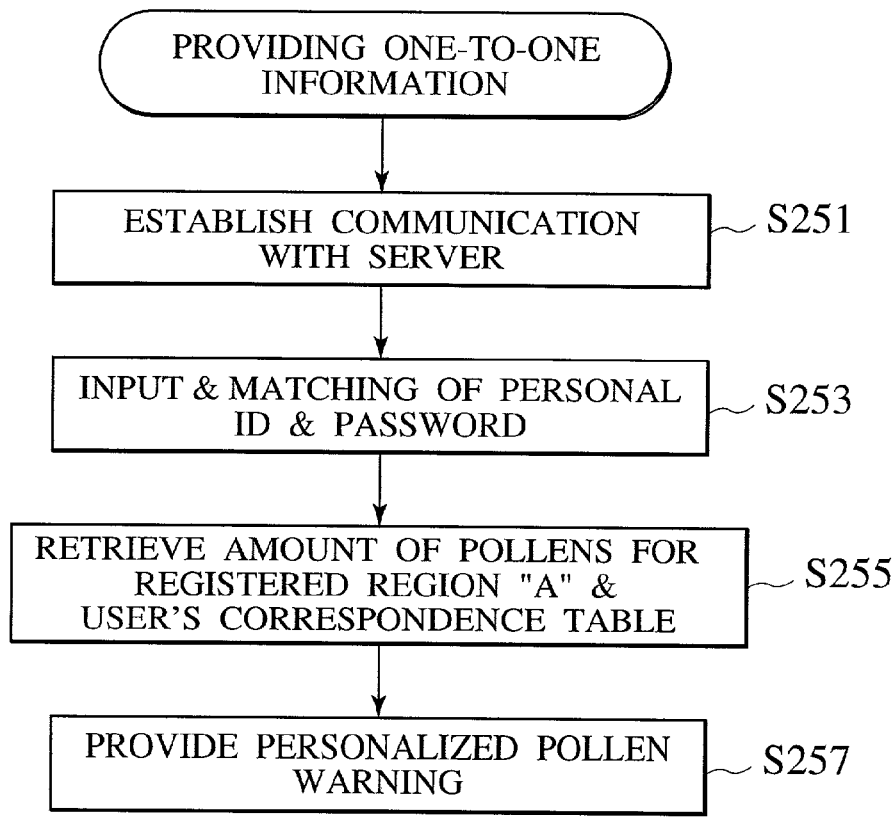
FIG. 16 is a flow chart showing a processing procedure for providing one-to-one information in the environmental information providing system of FIG. 7.
FIG. 17 is a diagram showing an exemplary correspondence table used in the processing for providing one-to-one information shown in FIG. 16.

Then, the information processing unit 255 searches through the pollen information database 253 according to the information on the user specified region A to obtain the pollen amount level at the user specified region A, judges the user's pollen allergy symptom that corresponds to the obtained pollen amount level in the user's correspondence table, and provides the judged user's pollen allergy symptom as the pollen warning information as shown in FIG. 17 so as to notify it to the user (step S257).

Next, with references to FIG. 18 and FIG. 19, the practical manners of utilizing the pollen information providing system of this embodiment will be described.

Figure 18:
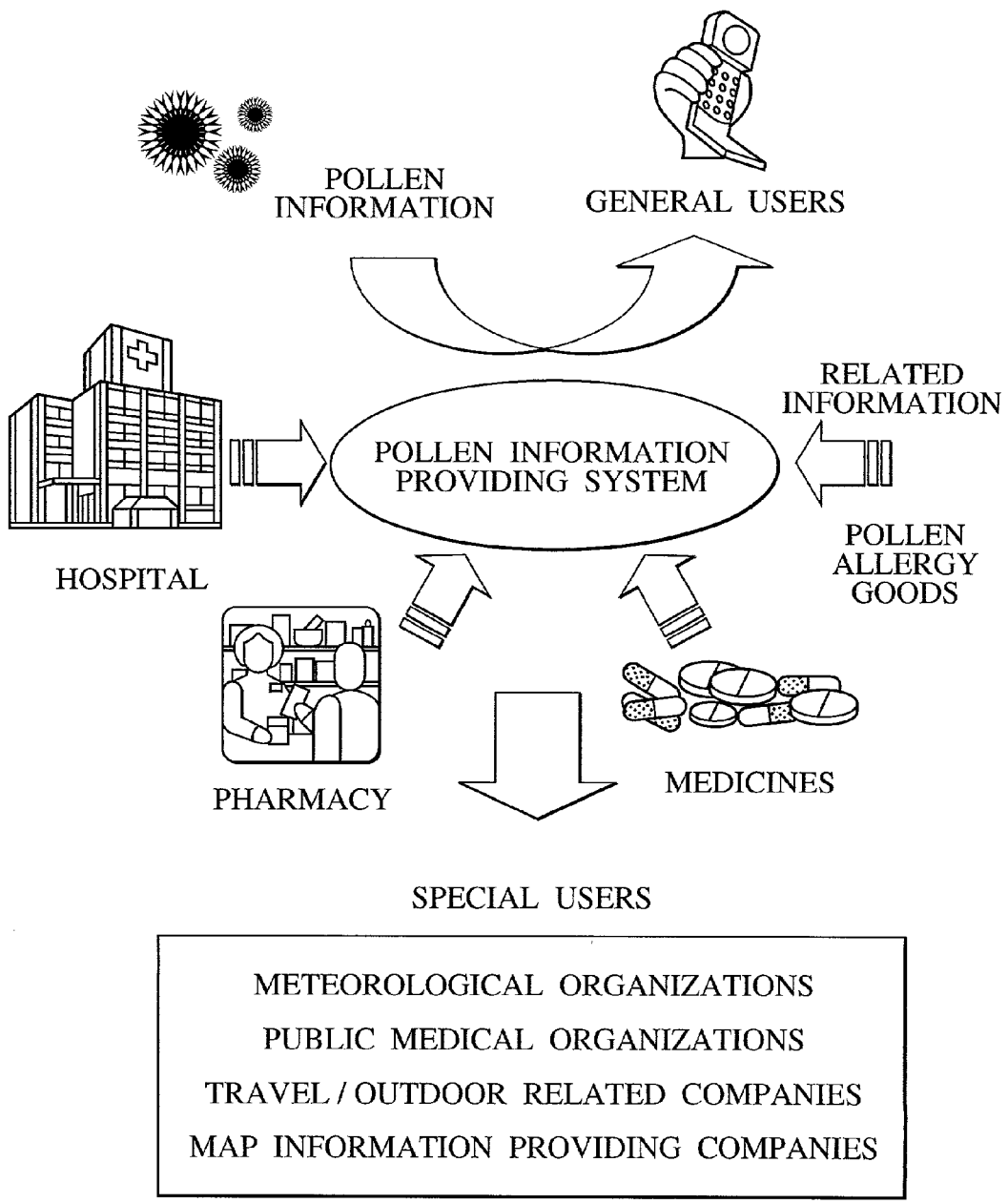
FIG. 18 is a diagram showing an environmental information market that can be formed around the environmental information providing system of the present invention.

FIG. 18 shows an exemplary pollen information market that can be formed around the pollen information providing system of this embodiment. In FIG. 18, the pollen information providing system can provide the pollen information not only to general users but also to special users such as meteorological organizations, public medical organizations, travel/outdoor related companies and map information providing companies. In addition, various related information such as information regarding the pollen allergy and information regarding medicines, and information regarding pollen allergy goods are entered from the hospital, pharmacy, etc., for example, and such a related information can also be provided to each user along with the pollen information.

Figure 19:
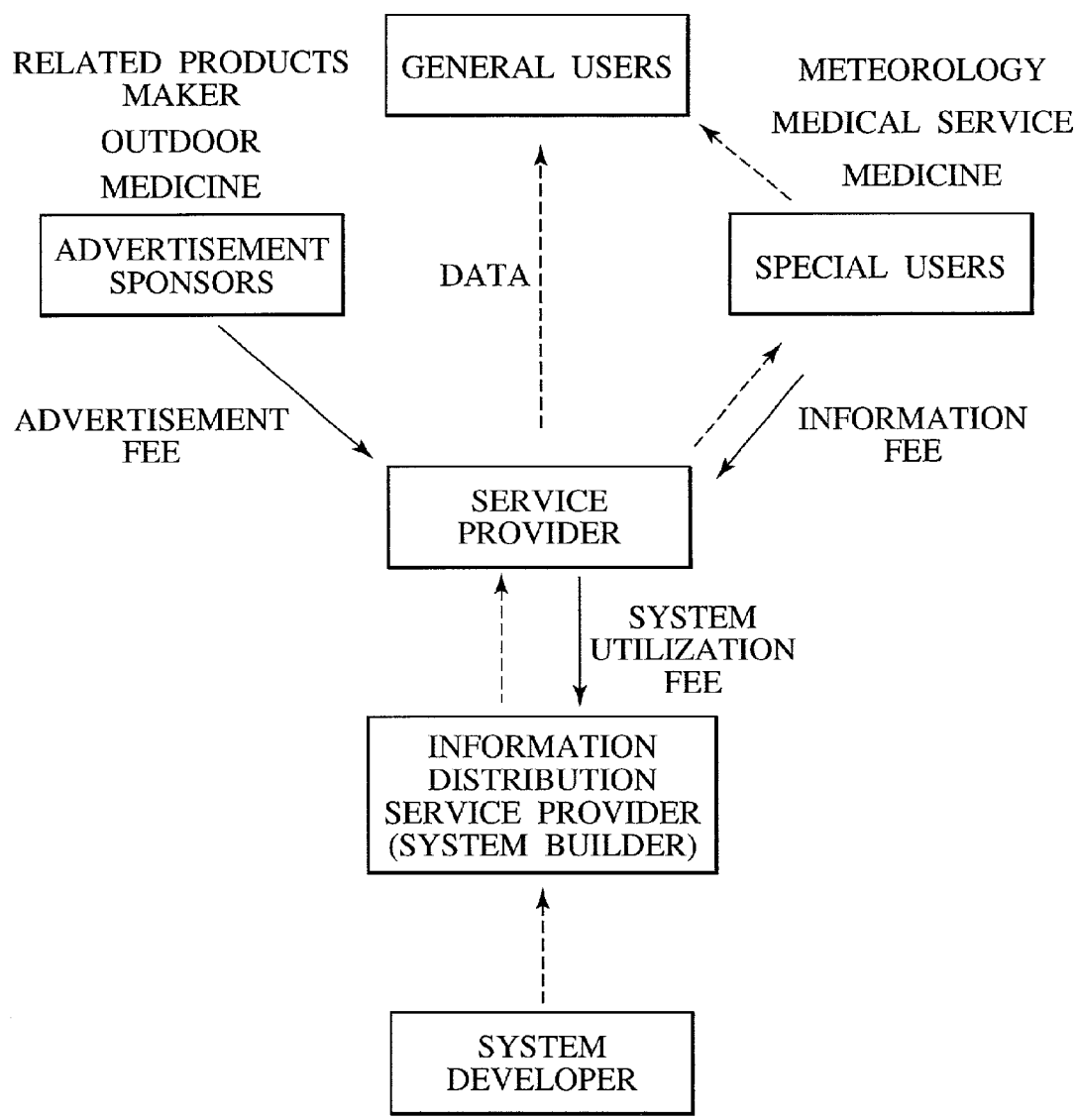
FIG. 19 is a diagram showing a service providing business environment that can be formed around the environmental information providing system of the present invention.

FIG. 19 shows an exemplary business environment for running a business of the pollen information providing service by using the pollen information providing system of this embodiment. In FIG. 19, the users of the pollen information providing services include general users (mass users) and special users such as specialized organizations or groups related to the meteorology, the medical service and the medicine. The information fee can be set free for the general users, while the advertisement fees are collected from the advertisement sponsors in exchange to the inclusion of the advertisements for the related services or goods. It is also possible to charge a fee for the one-to-one service or the warning service even to the general users. On the other hand, with respect to the special users such as specialized organizations or groups related to the meteorology, the medical service and the medicine, some information fee can be charged for the detailed information. These special users can have the additional value added to their existing services by adding this service as a new menu option.

The information distribution service provider may run this business by itself, but in the case where this is not possible due to some legal limitations, it is also possible to lease this system to a third party who wishes to run this business. In such a case, the facility investment can be recovered by collecting the system utilization fee from the third party service provider.

It is also possible to provide the personalized (one-to-one) information service as follows.

First, the personal information of the user is stored into the personal information database through the WWW server. Namely, a communication address of the user and data on the user's sensitivity with respect to the environment can be stored through the telephone line or the Internet from the communication device. For instance, information on evaluation of the pollen allergy symptoms in scale with five levels is registered into the personal information database from a portable telephone. The information processing unit on the server retrieves information on the pollen amount at the specified region and evaluates the pollen amount in scale with five levels. Then, the correspondence information indicating the correspondence between the five level evaluation of the pollen allergy symptoms and the five level evaluation of the pollen amount as shown in FIG. 15 described above is stored into the personal information database.

The pollen information stored in the pollen information database is disclosed on the Internet by the WWW server. The user can acquire this information easily by making an access to the WWW server through the telephone line and the Internet, for example, from the communication device. Also, by registering the personal information into the personal information database, the user can acquire the one-to-one information specific to the user based on the pollen allergy symptoms of the user.

Namely, the server creates a personal information site (page) with respect to the user who registered the personal information. The server then retrieves the correspondence table of the user, translates the current pollen amount into the corresponding pollen allergy symptom of the user according to the correspondence table, and writes it into the personal information site. The user can view the personal information site by entering the user ID and the password. In this way, different users can obtain different information according to their physical conditions, based on the pollen information indicating the same pollen amount at the same region.

This pollen information personalized for the individual user can be beneficially utilized as follows. The user can check the state of scattering pollens at a destination before actually visiting that destination. The state of scattering pollens is provided in a form translated into the expected pollen allergy symptom of each user, so that the user can make decisions regarding the activity by learning this information. In the case where the user must go to the destination, the user can take appropriate measures in advance according to the expected pollen allergy symptom.

There can also be a psychological effect of providing a sense of relief when the information indicates a preferable result. Also, the user may change a destination depending on this information. In the case of travel, the user may change visiting places or select the visiting places from the beginning, according to the pollen information for various places.

Also, by registering a region of interest, a threshold for the symptom level, and a communication address, etc., for the user in advance, it is possible to automatically notify the pollen allergy warning to the registered communication address when the pollen amount at that region that is translated into the pollen allergy symptom exceeds the registered threshold for the symptom level. This push type warning information is not an indiscriminate one based on the pollen amount alone, but rather an information that is only transmitted to the specific user according to the personal information of the user.

The pollen information distribution over the network can also provide a useful information service with respect to companies and public organizations. The market of anti-pollen allergy goods is largely affected by the state of scattering pollens. If areas with a large amount of scattering pollens can be comprehended in real time, supplies and stocks of goods can be managed accordingly. Also, the medicines for the pollen allergy are supplied through the pharmaceutical companies and public/private medical service organizations, and the demands for these medicines are also largely affected by the state of scattering pollens. The pharmaceutical companies and the medical service organizations can adjust supplies and stocks of the medicines according to the pollen information service.

On the other hand, this service can also be beneficial to the leisure related companies such as travel companies. For example, a travel agent can propose a travel plan according to the pollen information or provide some additional service to the traveller according to the pollen information. Also, a golf course or an amusement or theme park can provide some additional service according to the pollen information. Such an additional service can be useful in the competition with rivals.

Also, the user information of the personalized one-to-one information service can be utilized in collecting information on a market related to the pollen allergy. The collected pollen allergy market information can provide a useful database for the related companies in running business targeting at these users.

On the other hand, the information service provider may utilize this market information in running other businesses such as goods sales. Using this market information, it is possible to send appropriate advertisement on the pollen allergy related goods directly to the individual users according to the level of their pollen allergy symptoms. For instance, the advertisement on the pollen allergy related goods can be delivered along with the personalized pollen warning or pollen information described above.

This service can be viewed as a service for collecting, storing, processing, distributing and providing the pollen information, for which demands from a wide range of users including the medical service organizations, the pharmaceutical companies and the anti-pollen allergy goods makers can be expected. The pollen information can also be viewed as a kind of weather information as it relates to the atmosphere. The pollen information is also a regional information so that demands from the outdoor related companies such as those of travels and leisure activities can also be expected. Moreover, this service may be incorporated as a menu option in the map information providing service.

As described, according to this embodiment, it becomes possible for the user to acquire not only the real time raw pollen amount information for each region but also the statistically information processed pollen amount information regardless of distances appropriately and easily so that the convenience of the user can be improved.

Also, according to this embodiment, it becomes possible for the user to learn whether each region is in the state with a small pollen amount or in the state with a large pollen amount accurately, and in the case of travelling, for example, it is possible to take preventive measures prior to the travel by learning whether the visiting place is in the state with a large pollen amount or not in advance, so that the convenience of the user can be improved.

Also, according to this embodiment, it becomes possible for the user to learn the pollen distribution area information indicating areas with little pollens and areas with many pollens as well as a pollen border information accurately so that which regions are in the state with a large pollen amount can be ascertained from these information, which is convenient in the case of travelling, for example.

Also, according to this embodiment, even when the pollen amount level in the user's correspondence table is "small", for example, if the user's pollen allergy symptom corresponding to this pollen amount level is "slightly bad" in the correspondence table, the pollen warning information indicating "slightly bad" as the expected pollen allergy symptom of the user will be notified so that it becomes possible for the user to take the preventive measures against the pollens surely.

Also, according to this embodiment, it becomes possible for the user to learn in real time a change of the pollen amount state to the state with little pollens or the state with many pollens at a region specified by the user, so that the user can learn the arrival or the end of the pollen season very quickly.

Also, according to this embodiment, it becomes possible for the user to quickly acquire the pollen information at the currently located region, so that the user can take preventive measures against pollens surely before the pollen allergy gets worse.

Figure 20:
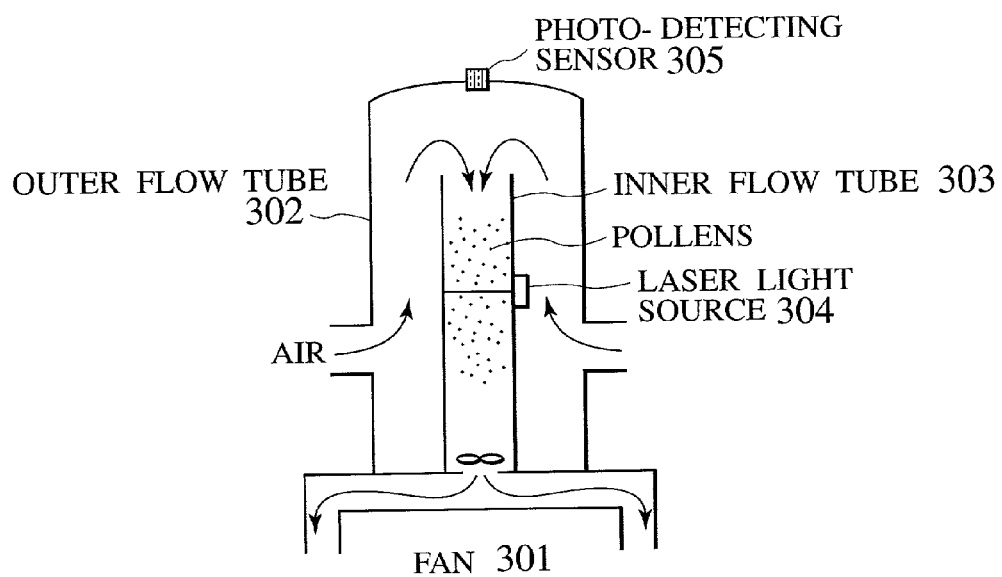
FIG. 20 is a schematic diagram showing an exemplary configuration of a pollen sensor that can be used in the environmental information providing system of the present invention.
Figure 21:
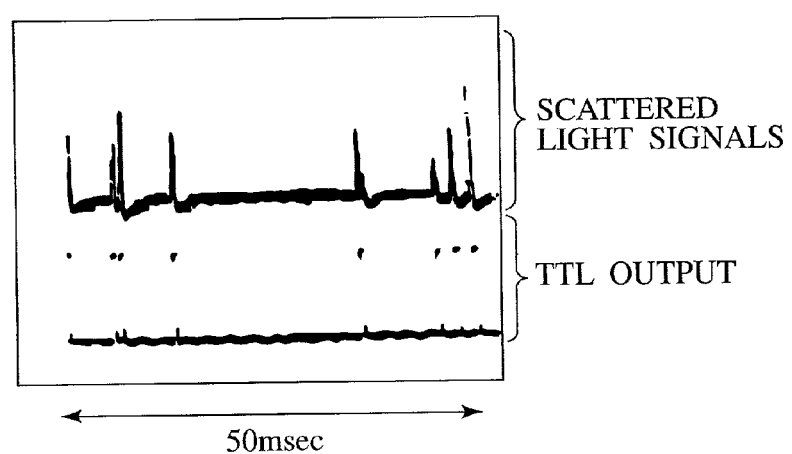
FIG. 21 is a diagram showing exemplary output signals of the pollen sensor of FIG. 20, for the purpose of explaining an operation principle of the pollen sensor of FIG. 20.

Referring now to FIG. 20 and FIG. 21, an example of the pollen sensor that can be used in the above described embodiments will be described.

FIG. 20 shows an exemplary configuration of the known pollen sensor which has a capability for capturing and counting spherical particles with approximately 30 micron diameter and the specific gravity of 1.2 to 1.3. This pollen sensor of FIG. 20 comprises: a fan 301 for inhaling the air and collecting floating particles contained in the air; an outer flow tube 302 for separating coarse particles from the collected floating particles, an inner flow tube 303 in which the pollen particles are to be detected from the remaining particles, a laser light source 304 for illuminating the pollen particles in the inner flow tube 303, and a photo-detecting sensor 305 for counting the pollen particles by detecting the laser beams reflected by the pollen particles.

In this pollen sensor, the fine particles with approximately 10 micron diameter or less, the pollen particles with approximately 30 micron diameter, and the coarse particles with approximately 50 micron diameter or more are separated by utilizing the fact that the motion of the particles in the flowing or static air changes depending on the diameter and the specific gravity of the particles.

Namely, in this pollen sensor, the pollen particles are separated from the floating particles in the air by utilizing the fact that the precipitation speed of the particles changes depending on the diameter and the specific gravity of the particles, by focusing attention on the precipitation of particles due to gravity which is one of the motions of particles in the air. In the following, the operation procedure of this pollen sensor of FIG. 20 utilizing the difference in the precipitation speeds of the particles will be described.

In the pollen sensor of FIG. 20, the air containing the floating particles in various diameters are introduced from an inlet provided on the outer flow tube 302 by the fan 301. At this point, the flowing speed of the air is set to be less than the precipitation speed of the coarse particles with approximately 50 micron diameter or more, such that the coarse particles precipitate in the outer flow tube 302 and are accumulated at a bottom of the outer flow tube 302 and not introduced into the inner flow tube 303.

The particles introduced into the inner flow tube 303 then precipitate in the inner flow tube 303 and pass through the laser beams emitted from the laser light source 304 provided inside the inner flow tube 303. As a result, the laser beams are scattered by the particles, and the scattered lights are detected by the photo-detecting sensor 3–5, where each scattered light corresponds to one particle.

FIG. 21 shows an exemplary measurement result of the scattered lights. In FIG. 21, signals shown in the upper half represent scattered light signals generated as the particles introduced into the inner flow tube 303 pass through the laser beams from the laser light source 304. The intensity of the scattered light signal depends on a size of the particle diameter in that the scattered light intensity is lower for the smaller particle diameter.

By utilizing this fact, the scattered lights with intensities below a threshold (0.2 to 0.3 V, for example) are removed by an electric filter in order to remove the scattered lights from fine particles with 10 micron diameter or less which are smaller than the pollen particles. Then, only the scattered lights with intensities above the threshold are processed into electric pulses at the TTL level as shown in the lower half of FIG. 21, and the pollen particles are counted by counting the TTL pulses generated during a certain period of time such as 30 minutes, for example.

It is to be noted that the communication systems that can be utilized in the above embodiments include portable telephones, Internet, digital satellite broadcasting, wired telephones, car navigation systems, displays inside trains, and displays within elevator compartment.

It is also to be noted that the environmental information that can be collected and provided in the above embodiments include information on diesel exhaust particles, NOX, ozone, nuclear radiations, oxygen density, carbon dioxide density, odor, ultraviolet rays, etc., as well as the conventional weather information (such as temperature, humidity, wind).

It is also to be noted that the personal health information that can be utilized instead of the pollen allergy symptoms in the above embodiments include pulse rates, blood pressures, and body temperatures.

This personal health information can be regularly uploaded to the server computer through the portable telephone or the like. At the server side, this personal information can be stored, managed, and presented to the user through the portable telephone or the like according to the needs of the user.

In addition, it is also possible to transmit an advise or alarm to the user through the portable telephone or the like when the value deviates significantly from an appropriate value. It is also possible to provide a service for automatically reporting to a medical service organization specified by the user when the abnormality is found in the stored data.

It is also to be noted that, besides those already mentioned above, many modifications and variations of the above embodiments may be made without departing from the novel and advantageous features of the present invention. Accordingly, all such modifications and variations are intended to be included within the scope of the appended claims.

What is claimed is:

1. A method for providing environmental information to users, comprising the steps of;
   collecting environmental information measured by a plurality of environment sensors arranged at a plurality of regions in a base device;
   storing the environmental information collected from the plurality of environment sensors in the base device;
   processing the environmental information in the base device according to user information of one of the users;
   providing processed environmental information from the base device to the user through a network connecting the users and the base device; and
   commanding a measurement condition setting update of all sensors in one of the plurality of regions for carrying out a measurement from the base device, when at least one environment sensor operated to carry out the measurement in the one of the plurality of regions measures a large amount of pollens.

2. The method of claim 1, wherein at the collecting step, the environmental information is collected through a radio communication system or a wired communication system connecting the environmental sensors and the base device.

3. The method of claim 1, wherein at the collecting step, each environment sensor transmits the environment information either automatically or in response to a request from the base device.

4. The method of claim 1, further comprising the step of:
   commanding a measurement condition setting update from the base device to at least one of the plurality of environment sensors when environmental information measured by the environment sensor meets a prescribed condition for judging a need for sensor measurement condition change.

5. The method of claim 1, wherein at the providing step, the base device provides the environmental information for a current location of the user which is registered by the user in advance or automatically detected according to a communication with the user, or the environmental information for a location close to the current location, in response to an information acquisition request made by the user through the network.

6. The method of claim 1, wherein at the collecting step, each environment sensor collects an amount of pollens scattering at the region in which each environment sensor is arranged, such that the base device processes pollen amount information to obtain pollen information at the processing step, and provides at least a portion of the pollen information at the providing step.

7. The method of claim 6, wherein at the processing step, the base device applies statistical information processing including integrating processing and averaging processing with respect to the pollen amount information collected from the environment sensors, such that the base device stores the pollen amount information and processed pollen amount information at the storing step.

8. The method of claim 6, wherein at the storing step, the base device stores the pollen amount information along with date and time information indicating date and time at which the pollen amount information is obtained, and
   the base device processes the pollen amount information for each region as a function of the date and time information at the providing step.

9. The method of claim 6, wherein at the processing step, the base device judges whether each region is in a state with little pollens or a state with many pollens, according to the pollen amount information, and
   the base device provides the pollen information indicating a state of each region as the state with little pollens or the state with many pollens at the providing step.

10. The method of claim 9, wherein at the processing step, the base device produces a pollen distribution area information indicating regions in the state with little pollens and regions in the state with many pollens in a form of a map, or a pollen border information indicating a border between the regions in the state with little pollens and regions in the state with many pollens on the map, and
    the base device provides the pollen information including the pollen distribution area information or the pollen border information at the providing step.

11. The method of claim 9, wherein the processing step includes the steps of:
    storing the pollen information indicating the state of each region in a pollen information database;
    storing the user information of each user including a user ID and a user specified region which are registered by each user, in a personal information database; and updating the pollen information database when the state of one of the plurality of regions has changed as a result of repeating the judging part of the processing step by using newly obtained pollen amount information, while searching through the personal information database to acquire user IDs of relevant users who registered said region that the state has been changed as the user specified region;

wherein the base device provides the pollen information for notifying a change of the state of said region that the state has been changed to the relevant users according to the user IDs acquired from the personal information database at the providing step.

12. The method of claim 6, wherein the processing step includes the steps of:

judging a pollen amount level of each region according to the pollen amount information for each region as one of a plurality of pollen amount levels, and storing the pollen amount level of each region in a pollen information database;

storing the user information of each user including a user ID, a user specified region, and a correspondence table indicating a correspondence between the plurality of pollen amount levels and a plurality of pollen allergy symptoms of each user which are registered by each user, in a personal information database;

searching through the pollen information database to acquire the pollen amount level of the user specified region of a selected one of the users, while searching through the personal information database to acquire the correspondence table of the selected user; and obtaining one pollen allergy symptom of the selected user that corresponds to the pollen amount level of the user specified region of the selected user acquired from the pollen information database according to the correspondence table of the selected user acquired from the personal information database;

wherein the base device provides the pollen information including a pollen warning information that indicates said one pollen allergy symptom to the selected user at the providing step.

13. The method of claim 1, further comprising applying information protection to the user information and the processed environmental information.

14. An environmental information providing system, comprising:

a first communication unit configured to collect environmental information measured by a plurality of environment sensors arranged at a plurality of regions;

a database configured to store the environmental information collected from the plurality of environment sensors by the first communication unit;

a processing unit configured to process the environmental information stored in the database according to a user information of one of a plurality of users;

a second communication unit configured to provide processed environmental information obtained by the processing unit to the user through a network connecting the users and the environmental information providing system; and a commanding unit configured to command a measurement condition setting update of all sensors in one of the plurality of regions for carrying out a measurement, when at least one environment sensor operated to carry out the measurement in the one of the plurality of regions measures a large amount of pollens.

15. The environmental information providing system of claim 14, wherein the first communication unit collects the environmental information through a radio communication system or a wired communication system connecting the environmental sensors and the environmental information providing system.

16. The environmental information providing system of claim 14, wherein each environment sensor transmits the environmental information either automatically or in response to a request from the environmental information providing system.

17. The environmental information providing system of claim 14, wherein the first communication unit also commands a measurement condition setting update to at least one of the plurality of environment sensors when environmental information measured by the environment sensor meets a prescribed condition for judging a need for sensor measurement condition change.

18. The environmental information providing system of claim 14 wherein the second communication unit provides the environmental information for a current location of the user which is registered by the user in advance or automatically detected according to a communication with the user, or the environmental information for a location close to the current location, in response to an information acquisition request made by the user through the network.

19. The environmental information providing system of claim 14, wherein the first communication unit collects pollen amount information from each environment sensor, the processing unit processes the pollen amount information to obtain pollen information, and the second communication unit provides at least a portion of the pollen information.

20. The environmental information providing system of claim 19, wherein the processing unit applies statistical information processing including integrating processing and averaging processing with respect to the pollen amount information collected from the environment sensors, and the database stores the pollen amount information and processed pollen amount information.

21. The environmental information providing system of claim 19, wherein the database stores the pollen amount information along with date and time information indicating date and time at which the pollen amount information is obtained, and the processing unit processes the pollen amount information for each region as a function of the date and time information.

22. The environmental information providing system of claim 19, wherein the processing unit judges whether each region is in a state with little pollens or a state with many pollens, according to the pollen amount information, and the second communication unit provides the pollen information indicating a state of each region as the state with little pollens or the state with many pollens.

23. The environmental information providing system of claim 22, wherein the processing unit produces pollen distribution area information indicating regions in the state with little pollens and regions in the state with many pollens in a form of a map, or a pollen border information indicating a border between the regions in the state with little pollens and regions in the state with many pollens on the map, and the second communication unit provides the pollen information including the pollen distribution area information or the pollen border information.

24. The environmental information providing system of claim 22, wherein the processing unit stores the pollen information indicating the state of each region in a pollen information database; stores the user information of each user including a user ID and a user specified region which are registered by each user, in a personal information database; and updates the pollen information database when a state of one of the plurality of regions has changed as a result of repeating the judging part of the processing step by using newly obtained pollen amount information, while searching through the personal information database to acquire user IDs of relevant users who registered said region that the state has been changed as the user specified region; and the second communication unit provides the pollen information for notifying a change of the state of said region that the state has been changed to the relevant users according to the user IDs acquired from the personal information database.

25. The environmental information providing system of claim 19, wherein the processing unit judges a pollen amount level of each region according to the pollen amount information for each region as one of a plurality of pollen amount levels, and stores the pollen amount level of each region in a pollen information database; stores user information of each user including a user ID, a user specified region, and a correspondence table indicating a correspondence between the plurality of pollen amount levels and a plurality of pollen allergy symptoms of each user which are registered by each user, in a personal information database; searches through the pollen information database to acquire the pollen amount level of the user specified region of a selected one of the users, while searching through the personal information database to acquire the correspondence table of the selected user; and obtains one pollen allergy symptom of the selected user that corresponds to the pollen amount level of the user specified region of the selected user acquired from the pollen information database according to the correspondence table of the selected user acquired from the personal information database; and the second communication unit provides the pollen information including a pollen warning information that indicates said one pollen allergy symptom to the selected user.

26. The environmental information providing system of claim 14, wherein the processing unit and the second communication unit apply an information protection to the user information and the processed environmental information.

\* \* \* \* \*